(12) United States Patent
Stibich

(10) Patent No.: US 11,511,007 B2
(45) Date of Patent: Nov. 29, 2022

(54) SYSTEMS WHICH DETERMINE OPERATING PARAMETERS FOR GERMICIDAL DEVICES

(71) Applicant: Xenex Disinfection Services Inc., San Antonio, TX (US)

(72) Inventor: Mark A. Stibich, Santa Fe, NM (US)

(73) Assignee: Xenex Disinfection Services Inc., San Antonio, TX (US)

( * ) Notice: Subject to any disclaimer, the term of this patent is extended or adjusted under 35 U.S.C. 154(b) by 0 days.

(21) Appl. No.: 17/005,509

(22) Filed: Aug. 28, 2020

(65) Prior Publication Data

US 2020/0390922 A1    Dec. 17, 2020

Related U.S. Application Data

(63) Continuation of application No. 15/653,035, filed on Jul. 18, 2017, now Pat. No. 10,772,980, which is a
(Continued)

(51) Int. Cl.
*A61L 2/24* (2006.01)
*A61L 2/10* (2006.01)
(Continued)

(52) U.S. Cl.
CPC .................... *A61L 2/24* (2013.01); *A61L 2/10* (2013.01); *G16H 40/20* (2018.01); *A61L 2/06* (2013.01);
(Continued)

(58) Field of Classification Search
CPC .......... A61L 2/10; A61L 2/24; A61L 2202/14; A61L 2202/16; A61L 2202/25
See application file for complete search history.

(56) References Cited

U.S. PATENT DOCUMENTS

| 2,182,732 A | 12/1927 | Meyer et al. |
| 2,215,635 A | 9/1940 | Collins |

(Continued)

FOREIGN PATENT DOCUMENTS

| CN | 87203475 | 8/1988 |
| CN | 2117167 | 9/1992 |

(Continued)

OTHER PUBLICATIONS

International Property Office, Examination Report for UK Patent Application No. GB1401483.1 dated Nov. 27, 2015, 3 pages.
(Continued)

*Primary Examiner* — Timothy C Cleveland
(74) *Attorney, Agent, or Firm* — Egan, Enders & Huston LLP.

(57) ABSTRACT

Systems are disclosed which include processor-executable program instructions for receiving data regarding characteristics of an area or a room and determining, based on the received data, operating parameter/s for one or more disinfection sources to disinfect the area/room. The data may include data regarding non-physical characteristics and/or physical characteristics of the area/room. In some embodiments, data regarding a quantity and/or type of at least a subset of the plurality of disinfection sources for disinfecting the room may also be considered for determining the operating parameter/s. In addition or alternatively, the data may be in relation to multiple disinfection sources in the area/room. In any case, a system is also disclosed which facilities power redirection among multiple disinfection sources upon detecting a given area has received a predetermined dose of ultraviolet light.

22 Claims, 7 Drawing Sheets

Related U.S. Application Data continuation of application No. 13/706,926, filed on Dec. 6, 2012, now Pat. No. 9,744,255, which is a continuation-in-part of application No. PCT/US2012/041483, filed on Jun. 8, 2012, which is a continuation of application No. 13/156,131, filed on Jun. 8, 2011, now Pat. No. 9,165,756.

(51) Int. Cl.
  *G16H 40/20* (2018.01)
  *A61L 2/06* (2006.01)
  *A61L 2/07* (2006.01)
  *A61L 2/14* (2006.01)
  *A61L 2/20* (2006.01)
  *A61L 2/22* (2006.01)

(52) U.S. Cl.
  CPC . *A61L 2/07* (2013.01); *A61L 2/14* (2013.01); *A61L 2/20* (2013.01); *A61L 2/22* (2013.01); *A61L 2202/14* (2013.01); *A61L 2202/25* (2013.01)

(56) References Cited

U.S. PATENT DOCUMENTS

| | | | |
|---|---|---|---|
| 2,382,939 A | 6/1944 | Koch | |
| 2,392,095 A | 1/1946 | Lemmers | |
| 2,615,120 A | 10/1952 | Macksoud | |
| 3,418,069 A | 12/1968 | Decupper | |
| 4,229,658 A | 10/1980 | Gonser | |
| 4,877,964 A | 10/1989 | Tanaka et al. | |
| 4,896,042 A | 1/1990 | Humphreys | |
| 5,023,460 A | 6/1991 | Foster, Jr. et al. | |
| 5,144,146 A | 9/1992 | Wekhof | |
| 5,220,734 A | 6/1993 | Carver | |
| 5,221,139 A | 6/1993 | Belfer | |
| 5,251,110 A | 10/1993 | Leleve | |
| 5,344,433 A | 9/1994 | Talmore | |
| 5,373,430 A | 12/1994 | McDermott | |
| 5,446,580 A | 8/1995 | Collins | |
| 5,613,261 A | 3/1997 | Kawakami et al. | |
| 5,744,094 A | 4/1998 | Castberg et al. | |
| 5,768,853 A | 6/1998 | Bushnell et al. | |
| 5,891,399 A | 4/1999 | Owesen | |
| 5,925,885 A | 7/1999 | Clark et al. | |
| 5,959,423 A | 9/1999 | Nakanishi et al. | |
| 6,203,060 B1 | 3/2001 | Cech et al. | |
| 6,242,753 B1 | 6/2001 | Sakurai | |
| 6,264,802 B1 | 7/2001 | Kamrukov et al. | |
| 6,264,836 B1 | 7/2001 | Lantis | |
| 6,398,970 B1 | 6/2002 | Justel et al. | |
| 6,403,030 B1 | 6/2002 | Horton, III | |
| 6,447,720 B1 | 9/2002 | Horton, III et al. | |
| 6,465,799 B1 | 10/2002 | Kimble et al. | |
| 6,493,087 B1 | 12/2002 | Fabinski et al. | |
| 6,539,727 B1 | 4/2003 | Burnett | |
| 6,566,659 B1 | 5/2003 | Clark et al. | |
| 6,656,424 B1 | 12/2003 | Deal | |
| 6,759,664 B2 | 7/2004 | Thompson et al. | |
| 6,774,382 B2 | 8/2004 | Yoshida | |
| 6,897,460 B2 | 5/2005 | Kobayashi et al. | |
| 6,911,177 B2 * | 6/2005 | Deal | A61L 2/10 422/62 |
| 6,932,494 B1 | 8/2005 | Burnett et al. | |
| 6,932,903 B2 | 8/2005 | Chang | |
| 6,962,239 B2 | 11/2005 | Shikai et al. | |
| 7,122,115 B2 | 10/2006 | Holt et al. | |
| 7,153,808 B2 | 12/2006 | Iwamoto et al. | |
| 7,175,806 B2 | 2/2007 | Deal et al. | |
| 7,251,853 B2 | 8/2007 | Park et al. | |
| 7,329,026 B1 | 2/2008 | Hayman et al. | |
| 7,371,351 B2 | 5/2008 | Goswami | |
| 7,380,627 B2 | 6/2008 | Huang et al. | |
| 7,423,367 B2 | 9/2008 | Lantis et al. | |
| 7,459,694 B2 | 12/2008 | Scheir et al. | |
| 7,476,006 B2 | 1/2009 | Hinds | |
| 7,498,004 B2 | 3/2009 | Saccomanno | |
| 7,638,090 B2 | 12/2009 | Hyde et al. | |
| 7,754,156 B2 | 7/2010 | Hyde et al. | |
| 7,829,867 B2 | 11/2010 | Hlavinka et al. | |
| 8,038,949 B2 | 10/2011 | Horne et al. | |
| 8,114,342 B2 | 2/2012 | Jung et al. | |
| 8,142,713 B2 | 3/2012 | Gordon | |
| 8,178,042 B2 | 5/2012 | Jung et al. | |
| 8,193,515 B2 | 6/2012 | Kreitenberg | |
| 8,203,126 B2 | 6/2012 | Rocha-Alvarez et al. | |
| 8,236,236 B2 | 8/2012 | Garner | |
| 8,277,724 B2 | 10/2012 | Jung et al. | |
| 8,354,057 B2 | 1/2013 | Heselton et al. | |
| 8,455,832 B2 | 6/2013 | Statham et al. | |
| 8,481,985 B2 | 7/2013 | Neister | |
| 8,575,567 B2 | 11/2013 | Lyslo et al. | |
| 8,895,939 B2 | 11/2014 | Lyslo et al. | |
| 9,023,274 B2 | 5/2015 | Garner et al. | |
| 9,093,258 B2 | 7/2015 | Stibich et al. | |
| 9,165,756 B2 | 10/2015 | Stibich et al. | |
| 9,744,255 B2 | 4/2017 | Stibich | |
| 10,092,665 B2 | 10/2018 | Lyslo et al. | |
| 10,406,254 B2 | 9/2019 | Garner et al. | |
| 10,729,797 B2 | 8/2020 | Lyslo et al. | |
| 10,772,980 B2 | 9/2020 | Stibich | |
| 2003/0085631 A1 | 5/2003 | Cech et al. | |
| 2003/0086821 A1 | 5/2003 | Matthews | |
| 2003/0137834 A1 | 7/2003 | Jigamian et al. | |
| 2004/0024278 A1 | 2/2004 | Megerle | |
| 2004/0052702 A1 | 3/2004 | Shuman et al. | |
| 2004/0140782 A1 | 7/2004 | Okabe et al. | |
| 2004/0175290 A1 | 9/2004 | Scheir et al. | |
| 2004/0202570 A1 | 10/2004 | Nadkarni | |
| 2004/0244138 A1 | 12/2004 | Taylor et al. | |
| 2005/0010331 A1 | 1/2005 | Taylor et al. | |
| 2005/0025662 A1 | 2/2005 | Lestician | |
| 2005/0058013 A1 | 3/2005 | Warf et al. | |
| 2005/0133740 A1 | 6/2005 | Gardner | |
| 2005/0151937 A1 | 7/2005 | Sugitani | |
| 2005/0171636 A1 | 8/2005 | Tani | |
| 2005/0186108 A1 | 8/2005 | Fields | |
| 2005/0276720 A1 | 12/2005 | Correa | |
| 2006/0009822 A1 | 1/2006 | Savage et al. | |
| 2006/0045817 A1 | 3/2006 | Horne et al. | |
| 2006/0143044 A1 | 6/2006 | Conry et al. | |
| 2006/0216193 A1 | 9/2006 | Johnson et al. | |
| 2006/0244403 A1 | 11/2006 | Christensson et al. | |
| 2006/0252326 A1 | 11/2006 | Mishler | |
| 2006/0261291 A1 | 11/2006 | Gardner | |
| 2006/0261772 A1 | 11/2006 | Kim | |
| 2006/0284109 A1 | 12/2006 | Scheir et al. | |
| 2006/0293794 A1 | 12/2006 | Harwig et al. | |
| 2007/0038206 A1 | 2/2007 | Altshuler et al. | |
| 2007/0140893 A1 | 6/2007 | McVey et al. | |
| 2007/0188113 A1 | 8/2007 | Okamoto | |
| 2007/0192986 A1 | 8/2007 | Garcia et al. | |
| 2007/0231188 A1 | 10/2007 | Jung et al. | |
| 2007/0231189 A1 | 10/2007 | Jung et al. | |
| 2007/0231190 A1 | 10/2007 | Hyde et al. | |
| 2007/0231192 A1 | 10/2007 | Jung et al. | |
| 2007/0231193 A1 | 10/2007 | Jung et al. | |
| 2007/0231194 A1 | 10/2007 | Jung et al. | |
| 2007/0231204 A1 | 10/2007 | Hyde et al. | |
| 2007/0253860 A1 | 11/2007 | Schroder | |
| 2008/0056933 A1 | 3/2008 | Moore et al. | |
| 2008/0085223 A1 | 4/2008 | Jung et al. | |
| 2008/0112845 A1 | 5/2008 | Dunn et al. | |
| 2008/0213128 A1 | 9/2008 | Rudy et al. | |
| 2008/0253941 A1 | 10/2008 | Wichers et al. | |
| 2008/0260601 A1 | 10/2008 | Lyon | |
| 2009/0123343 A1 | 5/2009 | Kwiatkowski | |
| 2009/0129974 A1 | 5/2009 | McEllen | |
| 2009/0191100 A1 | 7/2009 | Deal | |
| 2009/0208378 A1 | 8/2009 | Jung et al. | |
| 2009/0217547 A1 | 9/2009 | Kim et al. | |
| 2009/0228165 A1 | 9/2009 | Ozick et al. | |
| 2009/0232703 A1 | 9/2009 | Jung et al. | |

(56) References Cited

U.S. PATENT DOCUMENTS

| | | |
|---|---|---|
| 2009/0314308 A1 | 12/2009 | Kim et al. |
| 2009/0323181 A1 | 12/2009 | Andrews et al. |
| 2010/0026726 A1 | 2/2010 | Fujii |
| 2010/0032589 A1 | 2/2010 | Leben |
| 2010/0044319 A1 | 2/2010 | Engel et al. |
| 2010/0078574 A1 | 4/2010 | Cooper et al. |
| 2010/0082193 A1 | 4/2010 | Chiappetta |
| 2010/0086447 A1 | 4/2010 | Jung et al. |
| 2010/0090837 A1 | 4/2010 | Jung et al. |
| 2010/0104471 A1 | 4/2010 | Harmon et al. |
| 2010/0111775 A1 | 5/2010 | Hyde et al. |
| 2010/0183476 A1 | 7/2010 | Lu |
| 2010/0246169 A1 | 9/2010 | Anderson et al. |
| 2011/0002821 A1 | 1/2011 | Hyde et al. |
| 2011/0054574 A1 | 3/2011 | Felix |
| 2011/0206554 A1 | 8/2011 | Anderle et al. |
| 2011/0215261 A1 | 9/2011 | Lyslo et al. |
| 2011/0242823 A1 | 10/2011 | Tracy et al. |
| 2011/0305597 A1 | 12/2011 | Farren |
| 2012/0047763 A1 | 3/2012 | Abramovich et al. |
| 2012/0056102 A1 | 3/2012 | Stanley et al. |
| 2012/0093688 A1 | 4/2012 | Harmon et al. |
| 2012/0119108 A1 | 5/2012 | Goldshtein et al. |
| 2012/0126134 A1 | 5/2012 | Deal et al. |
| 2012/0223216 A1 | 9/2012 | Flaherty et al. |
| 2012/0305787 A1 | 12/2012 | Henson |
| 2012/0313532 A1 | 12/2012 | Stibich et al. |
| 2012/0315186 A1 | 12/2012 | Davis |
| 2013/0017122 A1 | 1/2013 | Jung et al. |
| 2013/0048876 A1 | 2/2013 | Crawford |
| 2013/0126760 A1 | 5/2013 | Klein et al. |
| 2014/0091044 A1 | 4/2014 | Jhawar et al. |
| 2015/0190540 A1 | 7/2015 | Stibich et al. |
| 2015/0320897 A1 | 11/2015 | Stibich et al. |

FOREIGN PATENT DOCUMENTS

| | | |
|---|---|---|
| CN | 2678651 | 2/2005 |
| CN | 2700714 | 5/2005 |
| CN | 1715793 | 1/2006 |
| CN | 201439877 | 4/2010 |
| CN | 201487874 | 5/2010 |
| CN | 201558350 | 8/2010 |
| CN | 201755324 | 3/2011 |
| DE | 149020 | 6/1981 |
| EP | 0252571 | 1/1988 |
| EP | 0566238 | 10/1993 |
| EP | 1588720 | 10/2005 |
| EP | 2172097 | 4/2010 |
| EP | 2174670 | 4/2010 |
| EP | 2314802 | 4/2011 |
| GB | 2203283 | 10/1988 |
| GB | 2452341 | 3/2009 |
| JP | 57-164062 | 10/1982 |
| JP | 60-63107 | 4/1985 |
| JP | 61-158455 | 7/1986 |
| JP | H01-221166 | 9/1989 |
| JP | 5-182635 | 7/1993 |
| JP | 6-63107 | 3/1994 |
| JP | H06-142175 | 5/1994 |
| JP | H07-289616 | 11/1995 |
| JP | H08-196606 | 8/1996 |
| JP | H10-246468 | 9/1998 |
| JP | H11-104224 | 4/1999 |
| JP | H11-216336 | 8/1999 |
| JP | 2001-340439 | 12/2001 |
| JP | 2002-000713 | 1/2002 |
| JP | 2002-191685 | 7/2002 |
| JP | 2003-135581 | 5/2003 |
| JP | 2003-262369 | 9/2003 |
| JP | 2004-073775 | 3/2004 |
| JP | 2005168858 | 6/2005 |
| JP | 2008036415 A1 | 2/2008 |
| JP | 2010-276737 | 12/2010 |
| JP | 2011-252612 | 12/2011 |
| KR | 20-0257478 | 12/2001 |
| KR | 10-2006-0097854 | 9/2006 |
| KR | 2006-0102300 | 9/2006 |
| KR | 20-2011-0003951 | 4/2011 |
| WO | 89/03778 | 5/1989 |
| WO | 94/06482 | 3/1994 |
| WO | 00/04430 | 1/2000 |
| WO | 01/06905 | 2/2001 |
| WO | 01-60419 | 8/2001 |
| WO | 02/058744 | 8/2002 |
| WO | 2005/082426 | 9/2005 |
| WO | 2006/070281 | 7/2006 |
| WO | 2007/001364 | 1/2007 |
| WO | 2007/020282 | 2/2007 |
| WO | 2007/081401 | 7/2007 |
| WO | 2007/089312 | 8/2007 |
| WO | 2008/144202 | 11/2008 |
| WO | 2011/088394 | 7/2011 |
| WO | 2011/055140 | 12/2011 |
| WO | 2012085250 A1 | 6/2012 |
| WO | 2012/142427 | 10/2012 |
| WO | 2014/022717 | 2/2014 |
| WO | 2014/039076 | 3/2014 |
| WO | 2014/088580 | 6/2014 |
| WO | 2014/100493 | 6/2014 |

OTHER PUBLICATIONS

Kowalski et al., "Mathematical Modeling of Ultraviolet Germicidal Irradiation for Air Distribution," Quantitative Microbiology 2, 2000, pp. 249-270.

International Property Office, Search & Examination Report for UK Patent Application No. GB1401483.1 dated Jul. 10, 2015, 7 pages.

International Preliminary Examining Authority, International Preliminary Report on Patentability for International Application No. PCT/US12/68216 dated Dec. 24, 2014, 4 pages.

International Property Office, Search & Examination Report for UK Patent Application No. GB1401483.1 dated Jul. 30, 2014, 5 pages.

International Searching Authority, Partial International Search Report for International Application No. PCT/US2012/041483 dated Dec. 10, 2012, 7 pages.

International Searching Authority, International Search Report & Written Opinion for Internation Application No. PCT/US2012/041483 dated Jul. 8, 2013, 25 pages.

International Searching Authority, International Search Report & Written Opinion for Internation Application No. PCT/US2012/068216 dated Sep. 26, 2013, 6 pages.

US Patent and Trademark Office, Office Action for U.S. Appl. No. 13/706,926 dated Jun. 26, 2015, 6 pages.

US Patent and Trademark Office, Office Action for U.S. Appl. No. 13/706,926 dated Nov. 3, 2015, 13 pages.

US Patent and Trademark Office, Final Office Action for U.S. Appl. No. 13/706,926 dated Jun. 10, 2016, 14 pages.

US Patent and Trademark Office, Notice of Allowance for U.S. Appl. No. 13/706,926 dated Feb. 3, 2017, 4 pages.

US Patent and Trademark Office, Notice of Allowance for U.S. Appl. No. 13/706,926 dated May 12, 2017, 4 pages.

US Patent and Trademark Office, Office Action for U.S. Appl. No. 15/653,035 dated Oct. 21, 2019, 3 pages.

US Patent and Trademark Office, Notice of Allowance for U.S. Appl. No. 15/653,035 dated May 11, 2020, 7 pages.

\* cited by examiner

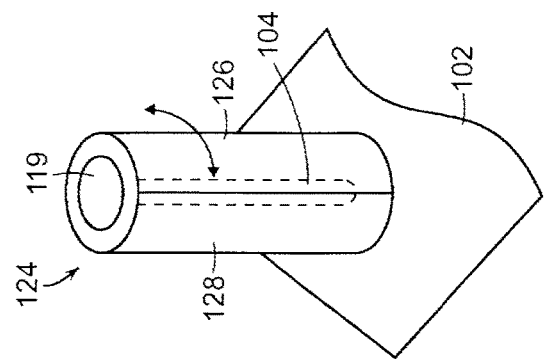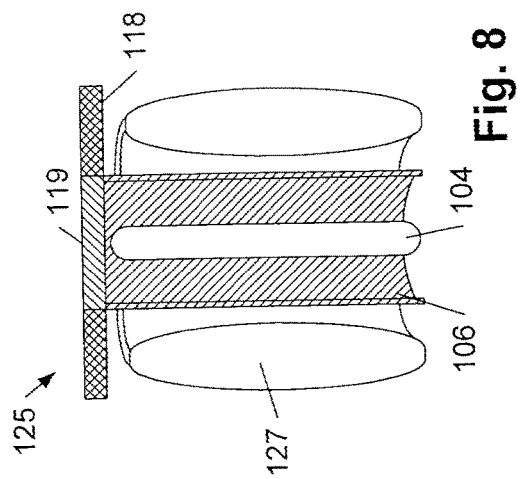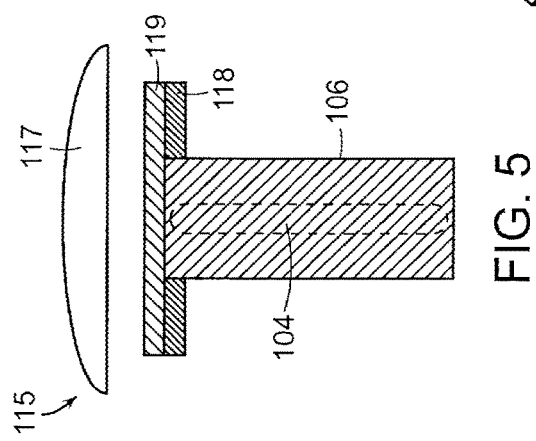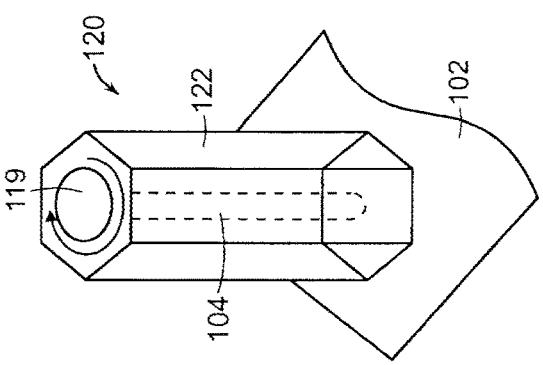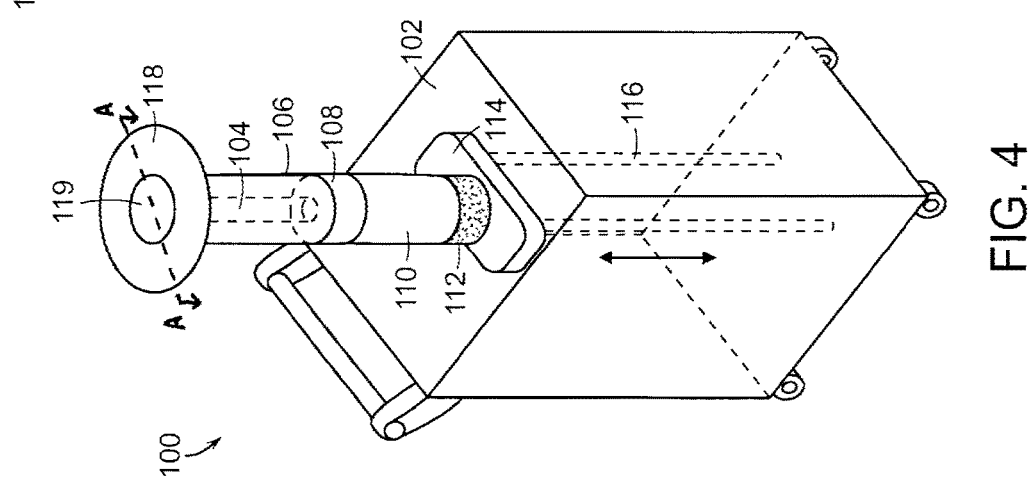

SYSTEMS WHICH DETERMINE OPERATING PARAMETERS FOR GERMICIDAL DEVICES

CONTINUING DATA

The present application is continuation of U.S. patent application Ser. No. 15/653,035 filed Jul. 18, 2017, which is a continuation of U.S. patent application Ser. No. 13/706,926 filed Dec. 6, 2012, now U.S. Pat. No. 9,744,255, which is a continuation-in-part from pending International Application No. PCT/US2012/041483 filed Jun. 8, 2012, which designates the United States and claims priority to U.S. application Ser. No. 13/156,131 filed Jun. 8, 2011, now U.S. Pat. No. 9,165,756.

BACKGROUND OF THE INVENTION

1. Field of the Invention

This invention generally relates to germicidal devices and, more specifically, systems which determine operating parameters and disinfection schedules for germicidal devices and further germicidal lamp apparatuses including lens systems.

2. Description of the Related Art

The following descriptions and examples are not admitted to be prior art by virtue of their inclusion within this section.

In general, germicidal systems are designed to subject one or more surfaces and/or objects to a germicide to deactivate or kill microorganisms residing upon the surface/s and/or object/s. Applications of germicidal systems include but are not limited to sterilization, object disinfection, and room/area decontamination. Examples of sterilizing systems are those used for sterilizing surgical tools, food or pharmaceutical packaging. Examples of area/room decontaminations systems are those used in hospital rooms to disinfect the surfaces and objects therein and those used in agricultural operations, such as those which are used to breed and/or farm animals. Area/room disinfection is becoming increasingly important as pathogenic microorganisms have been shown to be present in environments and cause infections. This is especially important as antimicrobial resistant organisms are more commonly found in environments and are becoming increasingly difficult to treat.

A challenge with conventional room/area decontaminations systems is getting a germicidal agent distributed in an efficient manner to all surfaces which need to be disinfected. In particular, many conventional room/area decontamination systems are limited in the number of disinfection sources they include due to cost and size restraints. In addition, the directionality of a germicidal agent in conventional room/area decontamination systems is often fixed. As a result, conventional systems often are configured to deliver a high dose of a germicidal agent such that a high number of surfaces within a room or area may be disinfected at the same time. A problem with a high dose blanket distribution of a germicidal agent is that some portions of a room or area may be overexposed, which effectively is a waste of the germicidal agent and potentially a waste of time and/or energy to perform a disinfection process. Furthermore, in some cases, portions of a room/area may not receive enough of a germicidal agent when the germicidal agent is blanket distributed throughout a room, particularly surfaces which are a relatively far distance from a disinfection source and/or which are not in direct line with a disinfection source. Underexposure of a germicidal agent can leave a surface or object with an undesirably high number of pathogenic microorganisms, leaving persons in subsequent contact with the surfaces highly susceptible to infection.

A further problem with conventional room/area decontamination systems is a lack of consideration and precedence of objects and surfaces in a room in performing a disinfection process. As a consequence, if a disinfection process for a room/area is terminated before its allotted time, there is potential that objects and/or surfaces within the room which are likely to be highly contaminated will not have been adequately disinfected. In particular, a disinfection source of room/area decontamination system is often positioned or installed near a central point in a room (rather than near one or more particular objects) such that germicidal exposure from the source to peripheries of the room/area is substantially uniform throughout the room/area. Similarly, in cases in which a system includes multiple disinfection devices, the devices are often distributed uniformly throughout the room rather than near one or more particular objects in an effort to disinfect the entire room in a given disinfection process.

In some embodiments, a disinfection source of a room/area decontamination system may be positioned near an object or surface, such as a bed in a hospital room, but positioning a disinfection source near a particular object does not address disinfection needs of other objects or surfaces within a room/area considered likely to be highly contaminated, such as a door handle or a light switch in a room. Furthermore, when a disinfection source is fixedly installed in a particular position within a room, the effect of its location to a particular object is rendered moot if the object is moved. In cases in which a decontamination system includes disinfection source/s which are freely positionable within a room, the task of positioning the disinfection source/s is generally manual and, thus, is labor intensive and prone to placement error. Moreover, neither of these latter configurations involve analyzing the characteristics of the room (e.g., size, areal configuration and/or relative placement of objects therein) for placement of disinfection sources therein.

A number of different methods exist for disinfecting surfaces and objects, ranging from chemical methods, such as bleach, to advanced methods, such as ultraviolet (UV) disinfection. In particular, it is known that UV irradiation in the spectrum between approximately 200 nm and approximately 320 nm is effective in deactivating and, in some cases, killing microorganisms, giving reason to the use of ultraviolet light technology for disinfecting and/or sterilizing items. Some UV disinfection devices utilize a discharge lamp to generate ultraviolet light. In addition to being used for disinfection and sterilization applications, discharge lamps are used in a variety of applications to generate ultraviolet (UV) light, such as for example polymer curing. In general, discharge lamps refer to lamps which generate light by means of an internal electrical discharge between electrodes in a gas. The electrical discharge creates a plasma which supplies radiant light. In some instances, such as in mercury-vapor lamps, the light generated is continuous once the lamp is triggered. Other configurations of discharge lamps, which are often referred to as flashtubes or flashlamps, generate light for very short durations. Such discharge lamps are sometimes used to supply recurrent pulses of light and, thus, are sometimes referred to as pulsed light sources. A commonly used flashlamp is a xenon flashtube.

Although different types of discharge lamps have been investigated to provide UV light for different applications, little has been done to improve the efficiency of the ultraviolet light generated in apparatuses having discharge lamps, particularly with respect to the propagation of the ultraviolet light (i.e., distance and angle of incidence on a target object), the intensity of the ultraviolet light, and the duration of exposure of the ultraviolet light. A reason for such a lack of advancement is that many apparatuses having discharge lamps, such as food sterilization and single object disinfection devices, are configured to treat items placed in close proximity and in direct alignment with the lamp and, thus, little or no improvement in efficiency of the UV light may be realized by altering its propagation. Furthermore, many conventional single object disinfection devices utilizing flashlamps employ less than 10 pulses of the lamp and operate for less than 5 seconds and, thus, there has been little need to increase the efficiency of such pulses. Moreover, room/area decontamination systems are specifically designed to disperse light over a vast area and, thus, altering UV propagation from a system may hinder such an objective.

In addition, many apparatuses with discharge lamps are limited in application and versatility. For instance, many food sterilization and single object disinfection devices are self-contained apparatuses and are configured for treatment of specific items and, thus, do not generally include features which improve the versatility of the systems for treatment for other items or use in other applications. Furthermore, some apparatuses require time consuming and/or cumbersome provisions in order to protect a user from harm. For example, pulsed ultraviolet light technology generally utilizes xenon flashlamps which generate pulses of a broad spectrum of light from deep ultraviolet to infrared, including very bright and intense visible light. Exposure of the visible light and the ultraviolet light may be harmful and, thus, provisions such as containing the pulsed light within the confines of the apparatus or shielding windows of a room in which a room decontamination unit is used may be needed.

Accordingly, it would be beneficial to develop ultraviolet discharge lamp apparatuses having features which improve their utilization, including but not limited to features which improve the efficiency of the ultraviolet light generated, increase the versatility of the apparatuses, and reduce and/or eliminate time consuming and cumbersome provisions that are required by conventional systems. In addition, it would be beneficial to develop room/area decontamination systems which are more effective and more efficient than conventional room/area decontamination systems.

SUMMARY OF THE INVENTION

The following description of various embodiments of systems is not to be construed in any way as limiting the subject matter of the appended claims.

Embodiments of systems include multiple disinfection sources each having a set of one or more sensors for detecting physical characteristics of an ambient exterior to its respective disinfection source. The systems further include a processing subsystem with processor-executable program instructions for receiving data from the sets of one or more sensors regarding physical characteristics of areas in a room in relation to each of the multiple disinfection sources and, based on the received data, determining one or more individual operating parameters for the multiple disinfection sources.

Other embodiments of systems include multiple ultraviolet light disinfection sources, one or more ultraviolet light dose sensors and a processing subsystem comprising processor-executable program instructions for receiving and tallying ultraviolet light dose measurements from at least one of the one or more ultraviolet light dose sensors that is associated with one of the multiple ultraviolet light disinfection sources. In addition, the processing subsystem includes program instructions for shutting off power to the one ultraviolet light disinfection source and redirecting the power to another of the multiple ultraviolet light disinfection sources upon determining the tallied ultraviolet light dose measurements meet or exceed a predetermined dose of ultraviolet light determined for the one ultraviolet light disinfection source.

Other embodiments of systems include multiple disinfection sources and a processing subsystem having processor-executable program instructions for receiving data regarding characteristics of an area or a room and receiving data regarding a quantity and/or type of one or more disinfection source of the multiple disinfection sources for disinfecting the area or room. In addition, the program instructions are for determining, based on the area/room characteristic data and the data regarding the quantity and/or type of the one or more disinfection sources, one or more operating parameters for at least one disinfection source of the one or more disinfection sources to disinfect the area or room.

BRIEF DESCRIPTION OF THE DRAWINGS

Other objects and advantages of the invention will become apparent upon reading the following detailed description and upon reference to the accompanying drawings in which:

FIG. 4 an isometric drawing of an ultraviolet discharge lamp apparatus having a vertically positioned discharge lamp;

FIG. 5 depicts an alternative configuration of a discharge lamp assembly for the ultraviolet discharge lamp apparatus depicted in FIG. 4;

FIG. 6 depicts an alternative configuration of an optical filter for the ultraviolet discharge lamp apparatus depicted in FIG. 4;

FIG. 7 depicts another alternative configuration of an optical filter for the ultraviolet discharge lamp apparatus depicted in FIG. 4;

FIG. 8 depicts a cross-sectional view of a variation of the ultraviolet discharge lamp apparatus depicted in FIG. 4 along axis AA, including a lens system adjacent to the optical filter;

Figure 1:
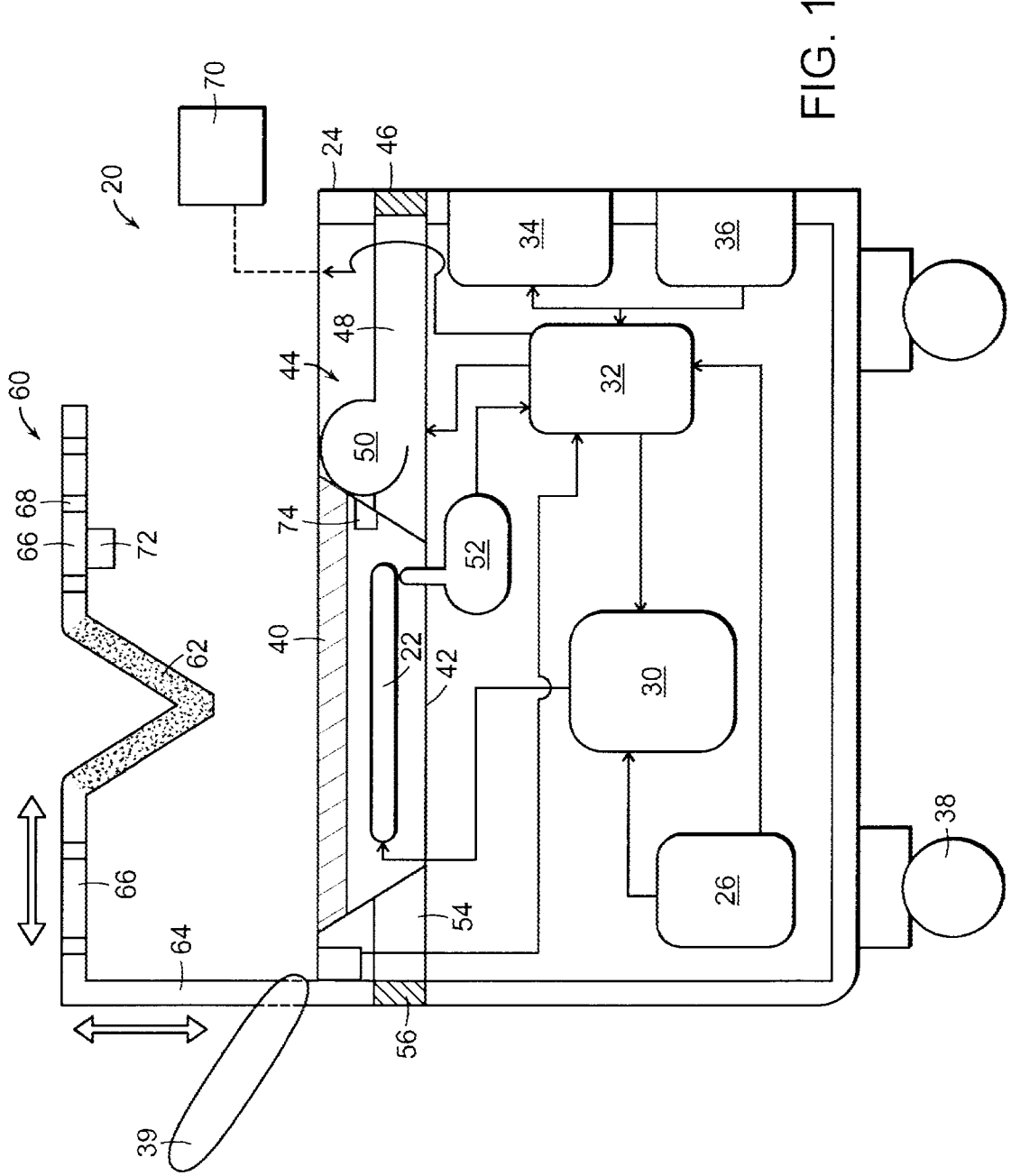
FIG. 1 is a cross-sectional schematic diagram of an ultraviolet discharge lamp apparatus having a horizontally positioned discharge lamp.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 2A:
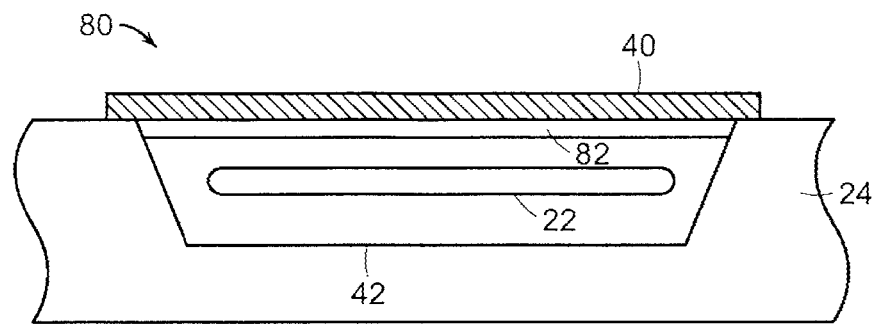
FIG. 2a depicts an alternative configuration for accommodating an optical filter in the ultraviolet discharge lamp apparatus depicted in FIG. 1.
Figure 2B:
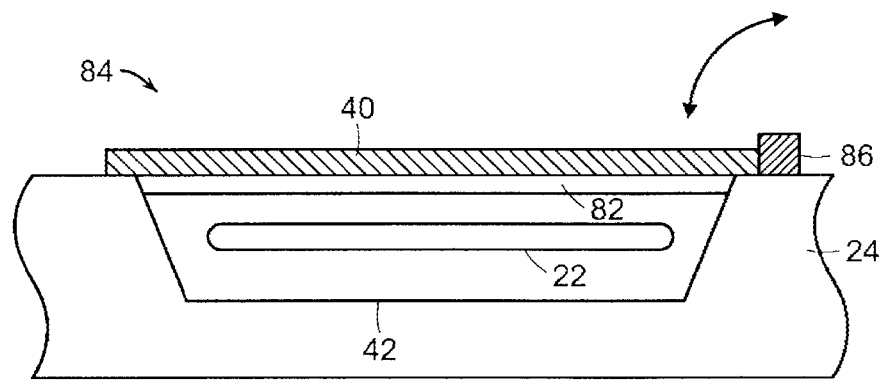
FIG. 2b depicts another alternative configuration for accommodating an optical filter in the ultraviolet discharge lamp apparatus depicted in FIG. 1.
Figure 2C:
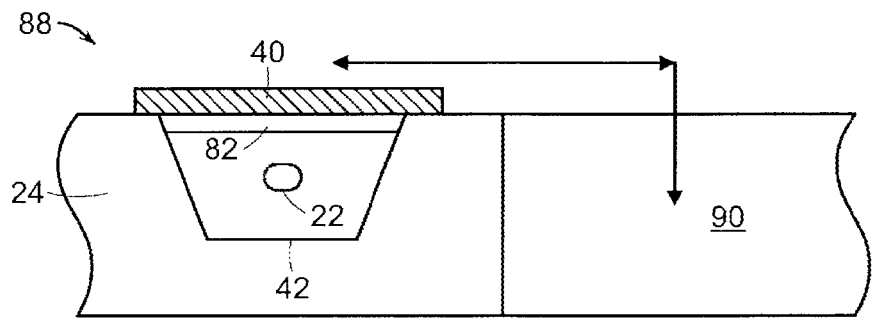
FIG. 2c depicts yet another alternative configuration for accommodating an optical filter in the ultraviolet discharge lamp apparatus depicted in FIG. 1.
Figure 3:
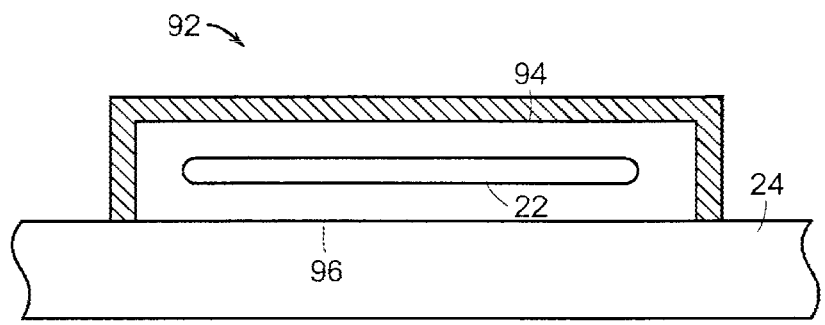
FIG. 3 depicts an alternative configuration of the ultraviolet discharge lamp apparatus depicted in FIG. 1 having a discharge lamp arranged exterior to a support structure of the apparatus.
Figure 9:
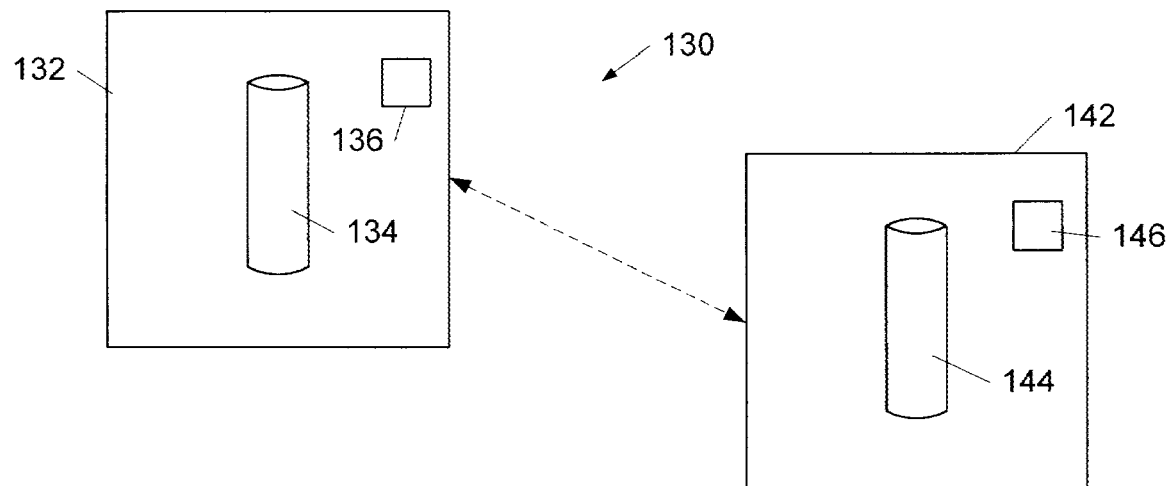
FIG. 9 depicts a system including multiple ultraviolet discharge lamp apparatuses.

Turning to the drawings, exemplary embodiments of discharge lamp apparatuses are provided. More specifically, exemplary configurations of apparatuses are shown in FIGS. 1-3 having a discharge lamp arranged lengthwise parallel to a plane of the apparatus at which the lamp is supported (hereinafter referred to as a "horizontally positioned lamp"). In addition, exemplary configurations of apparatuses are shown in FIGS. 4-8 having a discharge lamp arranged lengthwise perpendicular to a plane of the apparatus at which the lamp is supported (hereinafter referred to as a "vertically positioned lamp"). In addition, a system having two discharge lamp apparatuses is shown in FIG. 9. As will be set forth in more detail below, the apparatuses and features described herein are not limited to the depictions in the drawings, including that the discharge lamps are not restricted to "horizontal" and "vertical" positions. Furthermore, it is noted that the drawings are not necessarily drawn to scale in that particular features may be drawn to a larger scale than other features to emphasize their characteristics.

Each of the apparatuses described in reference to FIGS. 1-9 includes a discharge lamp configured to generate ultraviolet light and, thus, the apparatuses described in reference to FIGS. 1-9 are sometimes referred to as "ultraviolet discharge lamp apparatuses." In some embodiments, the discharge lamp of an apparatus may be further configured to generate other ranges of light, but such configurations will not deter from the reference of the apparatuses described herein as "ultraviolet discharge lamp apparatuses." In any case, the apparatuses described in reference to FIGS. 1-9 are absent of optics for producing a laser from light emitted from a discharge lamp and, accordingly, may be referred to herein as non-laser apparatuses in some embodiments. Alternatively stated, the apparatuses described in reference to FIGS. 1-9 are configured to propagate light emitted from the discharge lamp in a non-laser fashion. As set forth in more detail below, the apparatuses described in reference to FIGS. 1-9 are configured to expose areas and rooms as well as objects as a whole to ultraviolet light and, thus, are specifically configured to distribute light in a spacious manner rather than producing a narrow beam of limited diffraction as generated by lasers.

The term discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the discharge lamps which may be considered for the apparatuses described herein include gas-discharge lamps as well as surface-discharge lamps. Discharge lamps may be further characterized by the type of gas/es employed and the pressure at which they are operated. The discharge lamps which may be considered for the apparatuses described herein may include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof. Furthermore, the discharge lamps considered for the apparatuses described herein may be of any size and shape, depending on the design specifications of the apparatuses. Moreover, the discharge lamps considered for the apparatuses described herein may include those which generate continuous light and those which generate light in short durations, the latter of which are referred to herein as flashtubes or flashlamps. Flashtubes or flashlamps that are used to supply recurrent pulses of light are referred to herein as pulsed light sources.

A commonly used gas-discharge lamp used to produce continuous light is a mercury-vapor lamp, which may be considered for some of the apparatuses described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the apparatuses described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and killing of microorganisms.

Although they are not readily available on the commercial market to date, a surface-discharge lamp may be considered for some of the apparatuses described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp, and a surface discharge lamp in no way restrict the apparatuses described herein to include such lamps. Rather, the aforementioned descriptions and comparisons are merely provided to offer factors which one skilled in the art may contemplate when selecting a discharge lamp for an ultraviolet discharge lamp apparatus, particularly depending on the objective and application of the apparatus.

Although FIGS. 1-9 are specifically directed to ultraviolet discharge lamp apparatuses, it is noted that some of the components and configurations described for such apparatuses may be suitable for other types of germicidal lamp apparatuses, such as an apparatus including a high-intensity narrow-spectrum (HINS) lamp. In particular, the reflector systems described in reference to FIGS. 1, 4, 5 and 7 or variations thereof may be employed within other types of germicidal lamp apparatuses. In addition, the converging lens systems described in reference to FIG. 8 and variations thereof as well as the diverging lens systems described thereafter may be employed within other types of germicidal lamp apparatuses. Employing a reflector system and/or a lens system in other types of germicidal lamp apparatuses may generally depend on the size, shape, configuration and placement of the germicidal lamp and, thus, may vary significantly among systems. Furthermore, the system described in reference to FIG. 9 having a plurality of ultraviolet discharge lamp apparatuses may be applicable for a system including multiplicity of any type of germicidal lamp apparatuses.

As noted above, the apparatuses described in reference to FIGS. 1-9 are configured to distribute ultraviolet light in a spacious manner such that objects as whole and/or areas/rooms may be treated. In other words, the apparatuses described in reference to FIGS. 1-9 are not configured to produce a narrow beam of light for a specific small target as may be used for laser applications. Given their configuration to distribute ultraviolet light in a spacious manner, the apparatuses described in reference to FIGS. 1-9 may be particularly applicable for disinfecting, decontaminating and/or sterilizing objects as a whole as well as areas and/or rooms. For example, the apparatuses described in reference to FIGS. 1-9 may be used for disinfecting hospital rooms or may be used in agricultural operations, including those which are used to breed and/or farm animals. In addition or alternatively, the apparatuses described in reference to FIGS. 1-9 may be used for reducing microorganism growth on plants or sterilizing objects, such as surgical tools, food or pharmaceutical packaging. Other applications for the apparatuses described in reference to FIGS. 1-9 which involve spacious exposure to ultraviolet light may be polymer curing and medical procedures.

In some cases, the apparatuses described herein may be particularly directed to room disinfection. More specifically and as set forth in more detail below, some of the features presented for the apparatuses described in reference to FIGS. 1-9 (particularly the inclusion of an optical filter, the inclusion of a reflector system and/or a lens system to redirect ultraviolet light propagating from a support structure of the apparatus, the adaptation to move throughout a room during operation, and/or systems including multiple discharge lamp apparatuses) may be especially suitable for room disinfection apparatuses. For this reason, many of the apparatuses described in reference to FIGS. 1-9 are directed to room disinfection apparatuses. Furthermore, for reasons set forth below, many of the apparatuses described in reference to FIGS. 1-9 are specifically directed to floor based freestanding portable room disinfection apparatuses. The features described with regard to the apparatuses disclosed in reference to FIGS. 1-9, however, are not necessarily limited to room disinfection apparatuses or configurations to be floor-based, portable or freestanding. Rather, the features described in reference to FIGS. 1-9 may be applied in any type of ultraviolet discharge lamp apparatus. As used herein, the term room disinfection refers to the cleansing of a bounded area which is suitable for human occupancy so as to deactivate, destroy or prevent the growth of disease-carrying microorganisms in the area.

The room disinfection apparatuses described herein may come in a variety of configurations, including those which are floor based, wall based and ceiling based. However, although room disinfection apparatuses may be disposed within the ceiling of a room or within or against a wall, in many cases it is advantageous to position an ultraviolet room disinfection apparatus away from such structures. In particular, one of the primary factors affecting UV light intensity (and thus the disinfection efficiency of UV) on an object is distance to the object and, thus, in many cases it is advantageous to position an ultraviolet room disinfection apparatus near the center of a room or near objects suspected to be contaminated to minimize distances to objects. Moreover, in environments in which a room disinfection apparatus may be used in several rooms of a building (such as in a hospital), it is generally beneficial for the apparatus to be portable. For these reasons, many of the apparatuses described herein and depicted in the drawings are directed to freestanding, portable and floor-based room disinfection apparatuses.

In general, the apparatuses described in reference to FIGS. 1-9 may be configured to distribute light substantially unidirectionally or multi-directionally. As used herein, the phrase "configured to distribute light substantially unidirectionally" may refer to a configuration of an apparatus to propagate a majority of light emitted from a discharge lamp in a single direction with auxiliary light propagated at angles of less than 30 degrees from such a direction. All other distributions of light may be referenced for the phrase "configured to distribute light multi-directionally." Room disinfection apparatuses configured to distribute light substantially unidirectionally may be those disposed within a wall or a ceiling and/or which have a discharge lamp nested within the confines of the apparatus without an auxiliary optical component system to redirect light propagating away from the apparatus. In contrast, room disinfection apparatuses configured to distribute light multi-directionally may be those which have a discharge lamp extending out from a structure at which the discharge lamp is supported and/or which have an auxiliary optical component system to redirect light propagating away from the apparatus.

Given that a room generally includes objects of different sizes and shapes located at varying heights and distances from a given point in the room (giving rise to the number and varying location surfaces to be disinfected), it is sometimes advantageous for an ultraviolet apparatus used for room disinfection to be configured to distribute ultraviolet light in many directions (i.e., multi-directionally). Moreover, as noted above, it is sometimes advantageous to position an ultraviolet room disinfection apparatus away from room walls to reduce distances to the variety of objects in the room and effectively increase the disinfection efficiency of the UV light emitted from the apparatus. Further to such ideas, it is sometimes effective for an ultraviolet room disinfection apparatus to be configured such that at least some ultraviolet light generated by a discharge lamp is propagated to a region which encircles an exterior surface of the apparatus and further such that the ultraviolet light propagated to the encircling region during an operation of the apparatus collectively occupies the entirety of the encircling region. Such a configuration provides distinction from ultraviolet room disinfection apparatuses disposed in ceilings or walls and is described in more detail below in reference to some of the apparatuses depicted in the drawings.

Turning to FIG. 1, an exemplary configuration of an ultraviolet discharge lamp apparatus having a horizontally positioned lamp is provided. In particular, apparatus 20 is shown having discharge lamp 22 disposed within support structure 24 and specifically arranged lengthwise parallel to a plane of apparatus 20 at which discharge lamp 22 is supported (i.e., arranged parallel to an upper surface of support structure 24). As noted above and as will be set forth in more detail below, the ultraviolet discharge lamp apparatuses described herein are not restricted to embodiments in which a discharge lamp is arranged in a "horizontal position." Rather, the ultraviolet discharge lamp apparatuses described herein may include discharge lamps arranged at any angle relative to the surface plane of the support structure at which the discharge lamp is supported. Furthermore, the ultraviolet discharge lamp apparatuses described herein are not limited to embodiments in which a discharge lamp is arranged in proximity to an upper surface of an apparatus. In particular, the ultraviolet discharge lamp apparatuses described herein may have discharge lamps arranged in proximity to any exterior surface of an apparatus, including sidewalls and bottom surfaces.

Horizontally positioned and vertically positioned lamps arranged in proximity to upper surfaces of support structures are discussed herein in particularity since these were the configurations used to refine some of the novel features of the ultraviolet discharge lamp apparatuses disclosed herein. However, such disclosure should not be construed to necessarily limit the arrangement of discharge lamps in the ultraviolet discharge lamp apparatuses described herein. It is further noted that the ultraviolet discharge lamp apparatuses described herein are not restricted to embodiments in which a discharge lamp is nested within the confines of a support structure as depicted in FIG. 1. Rather, ultraviolet discharge lamp apparatuses may alternatively have a discharge lamp which is arranged at least partially exterior to a support structure, such as described for the exemplary embodiments depicted in FIGS. 3-8.

In addition to discharge lamp 22, apparatus 20 includes power circuit 26 and trigger circuit 30 disposed within support structure 24 as well as circuitry connecting the power circuit and trigger circuit to discharge lamp 22 as shown in FIG. 1. In general, power circuit 26, trigger circuit 30 and the connecting circuitry are configured to operate discharge lamp 22 (i.e., to send an electrical discharge to the lamp to create a radiating plasma therein). In particular, trigger circuit 30 is used to apply a voltage trigger voltage to an ignition electrode of discharge lamp 22, which may be wrapped around the lamp or may be the anode or cathode of the lamp, and power circuit 26 (e.g., a capacitor) is used to apply an electrical potential between the cathode and anode of the lamp. Trigger circuit 30 may, in some cases, be referred to herein as a pulse generator circuit, particularly when the discharge lamp apparatus includes a flash tube. The trigger voltage ionizes the gas inside the lamp, which increases the conductivity of the gas to allow an arc to form between the cathode and anode.

As noted above, in some cases, discharge lamp 22 may be a continuous light lamp, such as a mercury vapor lamp. In such embodiments, trigger circuit 30 may generally generate a signal of less than 1000 volts and, thus, may not be considered high voltage. (The term "high voltage" as used herein refers to voltages greater than 1000 volts.) In other embodiments, discharge lamp 22 may be a flash tube. Flash tubes require ignitions at higher voltages, generally between 2000 volts to 150,000 volts. An example of a voltage range of a trigger circuit for xenon bulb may be between about 20 kV and 30 kV. In comparison, an exemplary voltage range for a power storage circuit for a xenon bulb may be between approximately 1 kV and approximately 10 kV. In any case, apparatus 20 may include additional circuitry to provide power to other features in the apparatus, including but not limited to central processing unit (CPU) 32, user interface 34 and room occupancy sensor 36 as shown in FIG. 1.

Although it is not necessary, one or more operations of apparatus 20 may be computer operated and, thus, apparatus 20 may, in some embodiments, include CPU 32 to carry out applicable program instructions. In addition, apparatus 20 may optionally include user interface 34 to offer a means for a user to activate operation, and possibly particular operation modes, of apparatus 20 as well as offer a means for a user to access data collected from the apparatus. In some cases, user interface 34 may alternatively be a distinct device from apparatus 20 but configured for wired or wireless communication for apparatus 20. In this manner, apparatus 20 may be controlled remotely. Room occupancy sensor 36 is an optional safety mechanism, which may generally be configured to determine whether people are present in the room, such as by motion detection or photo recognition. Other optional features shown in apparatus 20 include wheels 38 and handle 39 to affect portability for the apparatus, but may be omitted depending on the design specifications of the apparatus.

As shown in FIG. 1, apparatus 20 may include optical filter 40, cooling system 44 and reflector system 60. As will be set forth in more detail below, the configuration of optical filters, cooling systems, lens systems and reflector systems as well as the placement of discharge lamps may vary among the ultraviolet light apparatuses described herein. In fact, alternative embodiments for one or more of such features are described in reference to FIGS. 2-8 relative to the configurations shown and described in reference to FIG. 1. Each of such embodiments include a support structure and accompanying components as described for FIG. 1, specifically in reference to support structure 22, power circuit 26, trigger circuit 30, CPU 32, user interface 34, room occupancy sensor 36, wheels 38 and handle 39. Such features, however, have not been depicted in FIGS. 2-8 for simplicity purposes as well as to emphasize the differing configurations of the depicted optical filters and reflector systems as well as the placement of discharge lamps.

As noted above, each of the apparatuses described in reference to FIGS. 1-9 includes a discharge lamp configured to generate ultraviolet light. In some embodiments, a discharge lamp of an apparatus may be further configured to generate other ranges of light, such as but not limited to visible light. In some of such cases, it may be advantageous to attenuate the visible light, particularly if (but not necessarily so limited) the generated visible light is very bright and/or distracting. For instance, xenon flashlamps generate pulses of a broad spectrum of light similar to the spectrum of sunlight, but the intensity of the visible light is up to 20,000 times higher than that of sunlight. As such, the apparatuses described herein may, in some embodiments, include an optical filter configured to attenuate visible light. In some cases, the apparatuses described herein may include an optical filter configured to attenuate light in a majority portion of the visible light spectrum, greater than 75% of the visible light spectrum, or the entire visible light spectrum. In other embodiments, however, the optical filter may be configured to attenuate light in less than a majority portion of the visible light spectrum. In any case, the optical filter may be configured to attenuate a majority amount of light in a given portion of the visible light spectrum and, in some cases, greater than 75% or all light in a given portion of the visible light spectrum.

Since the apparatuses described in reference to FIGS. 1-9 are configured for ultraviolet light exposure, the optical filter must pass ultraviolet light in addition to attenuating visible light. As such, in some cases, the optical filter may be visible light band-stop filter. In other embodiments, however, the optical filter may be an ultraviolet band-pass filter. In either case, the optical filter may be configured to pass a majority amount of light in a given portion of the ultraviolet light spectrum and, in some embodiments, greater than 75% or all light in a given portion of the ultraviolet light spectrum. In some cases, the given portion of the ultraviolet light spectrum may be a majority portion of the ultraviolet light spectrum, greater than 75% of the ultraviolet light spectrum, or the entire ultraviolet light spectrum. In other embodiments, however, the given portion of the ultraviolet light spectrum may be less than a majority portion of the ultraviolet light spectrum. In some embodiments, the optical filter may be specifically configured to pass light in a specific portion of the ultraviolet spectrum. For example, in cases in which the apparatus is used for disinfection, decontamination, or sterilization purposes, the optical filter may be configured to pass light in a majority portion, greater than 75%, or the entire portion of the germicidal UV spectrum (i.e., approximately 200-320 nm). In addition or alternatively, the optical filter may be configured to pass light in a majority portion, greater than 75%, or the entire portion of the ultraviolet light spectrum known to be optimally germicidal (i.e., approximately 260-265 nm).

An exemplary optical filter glass material which may be used as an optical filter for the ultraviolet discharge lamp apparatuses described herein is Schott UG5 Glass Filter which is available from SCHOTT North America, Inc. of Elmsford, N.Y. Schott UG5 Glass Filter attenuates a majority portion of the visible light spectrum while allowing approximately 85% of ultraviolet light in a range of approximately 260 nm to approximately 265 nm to pass. Other optical filter glass materials with similar or differing characteristics may be used as well, depending on the design specifications of an apparatus. In other cases, an optical filter considered for the ultraviolet discharge lamp apparatuses described herein may be a film having any of the optical characteristics described above. In such embodiments, the film may be disposed on an optically transparent material, such as quartz. In other embodiments, an optical filter considered for the ultraviolet discharge lamp apparatuses described herein may be a combination of an optical filter glass material and a film disposed thereon, each of which is configured to attenuate visible light.

The term "optical filter material" as used herein refers to a material designed to influence the spectral transmission of light by either blocking or attenuating specific wavelength spectrums. In contrast, the term "optically transparent" as used herein refers to a material which allows light to pass through without substantial blockage or attenuation of a specific wavelength spectrum. Quartz is a well known optically transparent material. The term "film" as used herein refers to a thin layer of a substance and is inclusive to the term "coating" which refers to a layer of a substance spread over a surface. Films considered for the optical filters described herein may be in solid or semi-solid form and, thus, are inclusive to solid substances and gels. In addition, films considered for the optical filter described herein may of liquid, semi-solid, or solid form when applied to a material, wherein the liquid and semi-solid forms may subsequently convert to solid or semi-solid form after application.

In any case, the efficiency of optical filters placed in the ultraviolet discharge lamp apparatuses described herein will decrease over time due to solarization and, thus, the optical filters may need to be periodically replaced. Solarization is a phenomenon pertaining to a decrease in an optical component's ability to transmit ultraviolet radiation in relation to its time of exposure to UV radiation. In some embodiments, an optical filter considered for the ultraviolet discharge lamp apparatuses described herein may include a rate of solarization that is approximately a whole number multiple of a degradation rate of the discharge lamp comprising an apparatus. Alternatively stated, the discharge lamp may have a rate of degradation that is an approximate factor of a rate of solarization of the optical filter. The term "factor" in such a characterization of the optical filter refers to the mathematical definition of the term, specifically referring to a number that divides another number evenly, i.e., with no remainder. The rate of solarization of an optical filter may be approximately any whole number multiple of a degradation rate of the discharge lamp including one and, thus, in some embodiments, a rate of solarization of an optical filter may be similar or the same as the rate of degradation of a discharge lamp.

In general, discharge lamps are warrantied to a number of uses (i.e., a particular number of triggers to generate a plasma), which is determined in accordance with the expected degradation of one or more of its components. For example, pulsed light sources are often warrantied to particular number of pulses. For the apparatuses described herein, such a use count could be used to characterize a degradation rate of a discharge lamp by multiplying the amount of ultraviolet light to be emitted during each operation times the number of triggers the discharge lamp is warrantied to be used. In this manner, a degradation rate may be computed which can be correlated to a solarization rate of an optical filter. If the solarization rate of an optical filter is approximately a multiple whole number of a degradation rate of a discharge lamp in an apparatus, the components may be advantageously replaced at the same time and, thus, downtime of the apparatus may be reduced relative to embodiments in which the components are replaced based on their individual merits. In addition, in cases in which light is monitored to determine when to replace the items, the monitoring process may be simplified in that light from only one component needs to be measured. Other features addressing solarization of the optical filter incorporated in the apparatuses described herein are discussed in more detail below in reference to FIGS. 1 and 3, specifically referencing a sensor system configured to monitor parameters associated with the operation of the discharge lamp as well as the transmittance of the optical filter and also inclusion of a thermal rejuvenation system within the apparatuses.

Several different exemplary configurations and arrangements of optical filters as well as optional accompanying components are described in detail below, particularly in reference FIGS. 1-8. More specifically, several different configurations of apparatuses are described below for accommodating an optical filter in alignment with a discharge lamp. Each of optical filters in the embodiments described in reference to FIGS. 1-8 may have the optical filter characteristics set forth above. The characteristics are not reiterated for each embodiment for the sake of brevity. As noted above, although it is not necessarily so limited, an optical filter may be especially suitable for a room disinfection apparatus. This is because room disinfection apparatuses are generally configured to distribute light into the environment of the apparatus and, thus, do not include a housing to contain the light. It is noted that although the inclusion of an optical filter may be beneficial in some of the apparatuses described herein, it is not necessarily a requirement and, thus may be omitted in some embodiments.

Another distinctive feature presented for the ultraviolet discharge lamp apparatuses described herein is a reflector system configured to redirect ultraviolet light propagating away from a support structure of an apparatus. In general, the reflector systems considered for the ultraviolet discharge lamp apparatuses described herein may be used to increase the size of an area exposed to ultraviolet light by the apparatus, decrease the distance ultraviolet light is propagated to target objects or areas, and/or improve the incidence angle of ultraviolet light on target objects or areas. Several different exemplary configurations and arrangements of reflector systems configured to accomplish one or more of such objectives are described in more detail below and are shown in FIGS. 1-8. In particular, apparatuses having a repositionable reflector are described. In addition, apparatuses having a reflector system which is configured to redirect ultraviolet light propagating away from a support structure of the apparatus to encircle an exterior surface of the apparatus are described. As noted above, such a configuration may be particularly applicable for room disinfection apparatuses.

Furthermore, apparatuses are described which have a reflector system configured to redirect ultraviolet light propagating away from a support structure of an apparatus to a region exterior to the apparatus and which is between approximately 2 feet and approximately 4 feet from a floor of a room in which the apparatus is arranged. In general, the region between approximately 2 feet and approximately 4 feet from a floor of a room is considered a "high touch" region of a room since objects of frequent use are generally placed in such a region. Examples of objects typically found in a high touch zone of a room include but are not limited to desktops, keyboards, telephones, chairs, door and cabinet handles, light switches and sinks. Examples of objects in high touch zones of hospital rooms additionally or alternatively include beds, bedside tables, tray tables and intravenous stands. Due to such a region being considered a high touch zone, it is generally considered the area of highest probability to come in contact with germs and some studies indicate that the high touch zone may be the area having the highest concentration of germs. For such reasons, it may be advantageous to direct at least some ultraviolet light to a region which is between approximately 2 feet and approximately 4 feet from a floor of a room. The inclusion of a reflector system as described herein may be used to attain such an objective.

Although it is not necessarily so limited, the reflector systems described herein may be especially suitable for a room disinfection apparatus. This is because room disinfection apparatuses are generally configured to distribute light into the environment of the apparatus and, thus, do not include a housing to contain and reflect the light. For reasons set forth above, many of the ultraviolet discharge lamp apparatuses described herein and depicted in the drawings are directed to floor based room disinfection apparatuses wherein the discharge lamp is arranged to propagate light above an upper surface of the support structure of the apparatus. As noted above, such emphasized disclosure should not, however, be construed to necessarily limit the configurations of the ultraviolet discharge lamp apparatuses described herein. For instance, in embodiments in which a discharge lamp is arranged to propagate light adjacent to a sidewall surface of a support structure of an apparatus, the reflector system of the apparatus may include a reflector coupled to an uppermost portion of the sidewall surface and/or a reflector coupled to a lowermost portion of the sidewall surface such that ultraviolet light is reflected downward or upward to a concentrated area. In other cases in which a discharge lamp is arranged to propagate light below a lower surface of a support structure of an apparatus, the reflector system of the apparatus may include a reflector below the discharge lamp. Several other arrangements may be suitable as well, particularly to increase the size of an area exposed to ultraviolet light by the apparatus, decrease the distance ultraviolet light is propagated to target objects or areas, and/or improve the incidence angle of ultraviolet light on target objects or areas.

In any case, as described in more detail below, a reflector system considered for the apparatuses described herein may include one or more reflectors, which may be of any size or shape and may be arranged at any position within an apparatus to achieve the desired redirection of light. In addition, the material of the reflector/s may be any found suitable for the desired redirection of light. An exemplary reflector material found suitable for many of the apparatus configurations described herein is 4300UP Miro-UV available from ALANOD Aluminium-Veredlung GmbH & Co. KG. Another exemplary reflector material found suitable for many of the apparatus configurations described herein is GORE® DRP® Diffuse Reflector Material available from W. L. Gore & Associates, Inc. Other reflector materials may be additionally or alternatively used, depending on the design specifications of the reflection system. In any case, each of the embodiments of the reflection systems described in reference to FIGS. 1-8 may have the characteristics of the reflection systems set forth above. The characteristics are not reiterated for each embodiment for the sake of brevity. As with the inclusion of an optical filter in the apparatuses described herein, although the inclusion of a reflector system may be beneficial in some apparatuses, it is not necessarily a requirement and, thus, may be omitted in some embodiments. Furthermore, the features of an optical filter and a reflector system are not mutually exclusive or mutually inclusive for an apparatus and, thus, an apparatus may include one or both features.

Yet another distinctive feature presented for the ultraviolet discharge lamp apparatuses described herein is a lens system configured to redirect ultraviolet light propagating away from ultraviolet discharge lamp. In some cases, the lens systems considered for the ultraviolet discharge lamp apparatuses described herein may be configured to diverge light propagating away from the discharge lamp to increase the size of an area exposed to ultraviolet light by the apparatus. In other cases, the lens system may be configured to converge light propagating away from the discharge lamp to focus the ultraviolet light to a specific location. Different configurations and arrangements of lens systems are described in more detail below, an example of which is shown in FIG. 9. In any case, a lens system considered for the apparatuses described herein may include one or more lenses, which may be of any size, shape or configuration and may be arranged at any position within an apparatus to achieve the desired redirection of light. In addition, a lens system considered for the apparatuses described herein may include simple lens/es, complex lens/es or a combination thereof. As with the inclusion of an optical filter and a reflector system in the apparatuses described herein, although the inclusion of a lens system may be beneficial in some apparatuses, it is not necessarily a requirement and, thus, may be omitted in some embodiments. Furthermore, the feature of a lens system is neither mutually exclusive nor mutually inclusive with either an optical filter or a reflector system and, thus, an apparatus may include any combination of such features.

Turning back to FIG. 1, apparatus 20 includes optical filter 40 configured to attenuate visible light emitted from discharge lamp 22. The configuration of optical filter 40 to attenuate visible light emitted from discharge lamp 22 in FIG. 1 specifically pertains to the optical characteristics of the filter to attenuate visible light as well as the placement of the optical filter above and in alignment with discharge lamp 22. As shown in FIG. 1, optical filter 40 may be arranged flush with the upper surface of support structure 24 between the sidewalls of cup portion 42 such that optical filter 40 comprises a wall of an encasement enclosing discharge lamp 22. As described in more detail below, the apparatuses described herein include a cooling system for regulating the temperature of the discharge lamp and encasing the lamp within an enclosure offers an efficient manner to achieve a desired temperature. The use of optical filter 40 as a wall of an encasement of discharge bulb 22 may simplify the incorporation of the optical filter into apparatus 20 and, thus, may be beneficial in some design aspects. However, in some embodiments, it may be beneficial to have optical filter 40 distinct from an encasement of discharge lamp 22. For example, in some cases, it may be advantageous to be able to arrange an optical filter in and out of alignment with a discharge lamp, depending on the desired operation of the apparatus. Such a configuration is described in more detail below and exemplary variations of apparatus 20 to accommodate such a configuration are shown in FIGS. 2a-2c.

The cooling systems which may be considered for the apparatuses described herein may vary and may generally depend on the design specifications of the apparatus. Exemplary cooling systems which may be used include but are not limited to forced air systems and liquid cooling systems. Cooling system 44 shown in FIG. 1 is a forced air system including air inlet 46, air intake duct 48, fan 50, temperature sensor 52, air duct 54 and air outlet 56. In some cases, one or more of air inlet 46, air intake duct 48, air duct 54 and air outlet 56 may include air filters. In some embodiments, air duct 54 and/or air outlet 56 may additionally or alternatively include an ozone filter. In other cases, however, an ozone filter may be omitted from the apparatus. Ozone may generally be created as a byproduct from the use of discharge lamp 22, specifically if the lamp generates ultraviolet light of wavelengths shorter than approximately 240 nm since such a spectrum of UV light causes oxygen atoms of oxygen molecules to dissociate, starting the ozone generation process. Ozone is a known health and air quality hazard and, thus, the release of it by devices is regulated by the Environmental Protection Agency (EPA). It is also known that ozone is an effective germicidal agent and, thus, if the amount of ozone to be generated by a discharge lamp is lower than the EPA exposure limits for ozone, it may be beneficial to exclude an ozone filter from apparatuses including such a discharge lamp.

In any case, different configurations of outlet ducts for cooling system 44 may be considered for apparatus 20 as well as the other apparatuses described herein. For example, in some configurations, a cooling system may be configured with an air outlet on the lower portion of a sidewall of support structure 24 or on the bottom surface of support structure 24. Benefits of such alternative configurations include increased capacity for an ozone filter as well as reduced disturbance to the environment, particularly when an air outlet is positioned on the bottom surface of support structure 24. In any case, the apparatuses described herein may include a cooling system for the rest of the components within support structure 24. In some cases, the support structure cooling system may be integrated with cooling system 44 for discharge lamp 22. In other embodiments, however, the two cooling systems may be distinct. It is noted that although the inclusion of one or more cooling systems may be beneficial in some of the apparatuses described herein, it is not necessarily a requirement and, thus may be omitted in some embodiments.

As noted above, apparatus 20 may include reflector system 60. In general, reflector system 60 is configured to redirect ultraviolet light propagating away from support structure 24. The configuration of reflector system 60 to achieve such an objective involves the placement, shape, size and angle of reflector 62. In particular, discharge lamp 22 is arranged in apparatus 20 to propagate light above an upper surface of support structure 24, and, thus, reflector 62 is arranged above discharge lamp 22 to redirect the propagating ultraviolet light. In general, the redirection of the ultraviolet light reduces the distance ultraviolet light travels to objects adjacent to the apparatus, including underside surfaces of objects as well as top and sidewall surfaces of objects. In particular, the redirection of ultraviolet light via reflector 62 averts travel to surfaces above the apparatus (e.g., the ceiling of the room in which the apparatus is arranged) to get reflected back to objects adjacent to the apparatus. The averting of travel to surfaces above the apparatus also shortens the distance ultraviolet light needs to travel to be incident on the underside of objects (such as by via reflection from the floor of a room in which an apparatus is arranged). As such, reflector system 60 may include a reflector disposed above support structure 24 but spaced apart from the ceiling of the room in which the apparatus is arranged as shown for reflector 62 in FIG. 1. In some cases, however, reflector system 60 may include a reflector disposed within or on the ceiling of the room in which the apparatus is arranged.

In some cases, reflection system 60 may be configured to optimize the incident angle at which ultraviolet light is directed to object surfaces. For example, reflector 62 may be designed with a specific size and/or shape and/or may be repositionable such that an optimum incident angle upon an object may be obtained. Exemplary configurations in which reflector 62 is repositionable are discussed in more detail below. In any case, reflector system 60 may, in some embodiments, include one or more additional reflectors (i.e., in addition to reflector 62). For example, in some cases, reflector system 60 may include a reflector coupled to a sidewall of support structure 24, which is configured to redirect ultraviolet light received from reflector 62. The inclusion of such an additional reflector may be beneficial for directing ultraviolet light to undersides of objects within a room. Additional reflectors may be used as well or alternatively and may generally be designed (i.e., size, shape and placement) to achieve any one of the objectives noted above for reflector system 60 in conjunction with reflector 62.

In some embodiments, reflector system 60 may be specifically configured to redirect ultraviolet light propagating away from support structure 24 to a region which is between approximately 2 feet and approximately 4 feet from a floor of a room in which apparatus 20 is arranged. In particular, as set forth above, it may be advantageous to redirect ultraviolet light to such a region since it is a high touch zone. In some cases, reflector system 60 may be additionally or alternatively configured to redirect ultraviolet light propagating away from support structure 24 to a region which encircles an exterior surface of the apparatus. For instance, reflector 62 may be of a shape and size such that ultraviolet light is redirected to a region encircling support structure 24. Alternatively, reflector 62 may be of a shape and size such that ultraviolet light is redirected to a region encircling reflector system 60. In either case, a conical shape for reflector 62 may be particularly suitable to achieve such redirection.

The term "encircle" as used herein refers to the formation of a continuous circle around an object. The term is not restricted to embodiments of surrounding an entirety of an object or even a major portion of an object. Thus, the phrasing that the ultraviolet discharge lamp apparatuses described herein may be configured such that ultraviolet light encircles an exterior surface of an apparatus refers to the formation of a continuous ring of ultraviolet light around at least some exterior portion of the apparatus. In addition, the phrasing that the ultraviolet discharge lamp apparatuses described herein may be configured such that ultraviolet light propagated to a region encircling an apparatus during an operation of the apparatus collectively occupies the entirety of the encircling region refers to each part of a continuous ring region around an apparatus being exposed to ultraviolet light at some time during the operation of the apparatus.

Regardless of the configuration of reflection system 60 or whether apparatus 20 even includes reflection system 60, apparatus 20 may, in some embodiments, include another reflector system arranged within support structure 24 which is configured to redirect light emitted from discharge lamp 22 in the direction of light propagation away from the support structure. In particular, apparatus 20 may include a reflection system which is configured to redirect light emitted from the side and bottom surfaces of discharge lamp 22 in the same direction as the light emitted from the top surfaces of discharge lamp 22. An example of such a reflection system may involve the floor and/or sidewalls of cup portion 42 having a reflective material. Other configurations of reflection systems, however, may be considered for the apparatuses described herein.

As shown in FIG. 1, reflector system 60 may include support beams 64 and 66 to suspend reflector 62. Such a cantilever support structure is merely an example and various other support structures may be considered for reflector 62. Regardless of the configuration to suspend reflector 62 above discharge lamp 22, reflector system 60 may, in some cases, include through holes such that some light propagated toward reflector system 60 may pass through to regions above reflector system 60. An example of an embodiment is shown in FIG. 1 with support beam 66 including through holes 68. In additional or alternative cases, reflector 62 may include through holes for such a purpose. In other embodiments, reflector system 60 may be void of such through holes. Regardless, the size of reflector system 60 and, more specifically, the size of reflector 62 may vary among apparatuses. In some cases, the areal dimensions of reflector 62 may be the same or larger than the areal dimensions of the encasement in which discharge lamp 22 is contained. In this manner, nearly all the light propagating from support structure 24 will be directed to reflector 62. In other embodiments, however, the areal dimensions of reflector 62 may be smaller than the areal dimensions of the encasement in which discharge lamp 22 is contained. In such cases, some light propagating from support structure 24 may be directed beyond reflector 62.

Regardless of its size and configuration, reflector system 60 may, in some cases, be configured to move reflector 62 in the horizontal and/or vertical direction as shown by the double-arrowed lines in FIG. 1. In this manner, reflector 62 may be a repositionable reflector. In some embodiments, reflector 62 may be moved between operations of apparatus 20 and, as such, reflector system 60 may, in some cases, include a means for securing the repositionable reflector at different positions within apparatus 20. In other embodiments, reflector system 60 may include a means for moving reflector 62 while apparatus 20 is in operation. The movement of reflector 62 may be continuous or periodic while apparatus 20 is in operation and, thus, reflector 62 may be moved while discharge lamp 22 is emitting light in some cases. The reference of apparatus 20 being in operation refers to periods when the components of the apparatus have been activated to operate discharge lamp 22 and specifically the operations by which to generate a radiating plasma within the discharge lamp. As noted above, discharge lamp 22 may, in some embodiments, be configured to generate continuous light once the lamp is triggered and, as such, the reference of apparatus 20 being in operation in such cases refers to the time used to trigger the lamp as well as the time of continuous light emission. In other embodiments, a flashlamp or a pulsed light source may be used for discharge lamp 22 and, in such cases, the reference of apparatus 20 being in operation refers to the times in which light is emitted from the lamp as well as times in between the light flashing.

In any case, a means for moving reflector 62 and sometimes securing reflector 62 at different positions within apparatus 20 may, in some embodiments, include linear actuator/s for beam 64 and/or beam 66 as well as program instructions processed by CPU 32 to affect the movement of the linear actuator/s and the timing thereof. In some embodiments, apparatus 20 may be configured such that reflector 62 may be moved manually. An exemplary means for securing reflector 62 at different positions within apparatus 20 in such cases may include notches along beam 64 and/or beam 66 and a receiving protrusion on reflector 62 or vice versa. Other various means for moving reflector 62 and/or securing reflector 62 at different positions within apparatus 20 may be considered as well and, thus, the apparatuses are not limited to the examples noted above. In any case, reflector 62 may be detachable from apparatus 20 in some cases to affect its movement relative to discharge lamp 22 and/or for ease of storage or portability of apparatus 20.

In some cases, the movement of reflector 62 may be based on characteristics of a room in which apparatus 20 is arranged. More generally, it may be advantageous, in some embodiments, to access and/or analyze the characteristics of a room and use such information to determine a number of operational parameters for apparatus 20, such as but not limited to the placement of reflector 62 and/or the movement characteristics of reflector 62. For example, if a relatively high number of objects within a room are in the same general area, it may be beneficial to position reflector 62 to direct more light to that area as compared to other areas in the room. Other examples of determining operational parameters of disinfection sources based on the characteristics of a room are described in reference to FIGS. 2a-2c (i.e., determining a position of optical filter 40 based on characteristics of a room), in reference to FIG. 7 (i.e., determining a position of the optical filter/reflector assembly based on characteristics of a room), in reference to FIG. 9 (i.e., determining a position of a lens relative to a discharge lamp), as well as in reference to FIGS. 11 and 12.

In general, the phrase "characteristics of a room" as used herein refers to physical attributes as well as non-physical attributes of a room. Non-physical attributes of a room include but are not necessarily limited to identifiers used to reference a room (e.g., room number and/or room name) and occupancy information regarding a room (e.g., infection information of a patient previously occupying the room or a patient scheduled to occupy the room). Physical attributes of a room include but are not necessarily limited to size and/or dimensions of the room and/or the number, size, distances, locations, reflectivity and/or identification of surfaces, objects and/or items within the room. In some cases, a physical attribute of a room may be the identification of one or more pathological organisms and, sometimes further the number or concentration of such organism/s in the room, in a particular region of the room, or on a particular surface in the room.

The phrase "operating parameter of a disinfection source" as used herein refers to any parameter which may affect operation of a disinfection source, including but not limited to run time of a disinfection source, position of a disinfection source, orientation of components comprising a disinfection source, germicidal dosing parameters for the disinfection source, and/or power supplied to a disinfection source. In cases in which the disinfection source includes a pulsed germicidal source, such as a flashlamp for example, germicidal dosing parameters for the disinfection source may include pulse duration and/or pulse frequency. Furthermore, in embodiments in which the germicidal source is a flashlamp, power supplied to the flashlamp may be referred to as "pulse intensity" or "intensity of the lamp". The term "disinfection source" as used herein refers to a collection of one or more components used to generate and disperse a germicidal agent, and, if applicable, is inclusive to any additional components used to effect the generation or dispersal of the germicidal agent. For example, discharge lamp 22, power circuit 26, trigger circuit 30, optical filter 40, and reflector system 60 of FIG. 1 may collectively be referred to as a disinfection source. Alternatively, apparatus 20 as a whole may be referred to as a disinfection source.

In some embodiments, apparatus 20 may include or may be configured to access a database listing characteristics of the room in which apparatus 20 is arranged. In addition or alternatively, apparatus 20 may include system 70 for collecting and/or generating data regarding characteristics of a room in which the apparatus is arranged. In such cases, any system known in the art for collecting, generating and/or analyzing characteristics of a room may be used, depending on the data to be generated. Examples include spatial sensors, photo recognition systems and/or dosimeters. As shown in FIG. 1, system 70 may, in some embodiments, be operationally coupled to CPU 32. Alternatively, CPU 32 may be configured to access room characteristic data from a database. In either case, CPU 32 may be configured to retrieve and access data regarding characteristics of the room in which apparatus 20 is arranged and determine an operating parameter of apparatus 20, such as a position of reflector 62, based on the data. In some embodiments, the determined operating parameter may be relayed via user interface 34 such that a user of apparatus 20 may be informed to invoke the operating parameter for apparatus 20, such as move reflector 62 to a particular position. In other cases, CPU 32 may be configured to send a command in accordance with the determined operating parameter to a means within apparatus 20 for automatically invoking the operating parameter, such as automatically moving reflector 62.

In some embodiments, system 70 may be used to measure doses of ultraviolet light received at an object or spot in a room in which apparatus 20 is arranged. In particular, measuring the dose of ultraviolet light received at an object or spot in a room may aid in determining operating parameter of apparatus 20, such as optimizing the placement of reflector 62. As noted above, one of the primary factors affecting UV light intensity on an object is distance to the object. Another primary factor is the angle of incidence of the light. In light thereof, if doses of ultraviolet light received at an object or spot in a room can be measured, such measurements can be used to determine operating parameter of apparatus 20 (e.g., move reflector 62 such as to optimize the angle of incidence on the object or spot). Through the operational coupling of system 70 to CPU 32, CPU 32 may be configured to retrieve measurements from system 70, determine an operating parameter of apparatus 20 based on the measurements, such as a position of reflector 62, and either relay the determined operating parameter to user interface 34 and/or send a command in accordance with the determined operating parameter to a means within apparatus 20 for automatically invoking the operating parameter, such as moving reflector 62. In general, any system known in the art for measuring ultraviolet light doses may be used for system 70. Examples include ultraviolet dosimeters and radiometers.

As noted above, the efficiency of discharge lamps and optical filters will decrease over time due to solarization. In addition, discharge lamps generally have a limited life as components thereof wear after a great deal of use. As such, the ultraviolet discharge lamp apparatuses considered herein may, in some embodiments, include a sensor system configured to monitor parameter/s associated with the operation of the discharge lamp and, if applicable, parameter/s associated with the transmittance of the optical filter. In particular, such a sensor system may be beneficial for determining when to replace the discharge lamp and, if applicable, the optical filter as well as monitoring the efficiency of the UV light emitted from the apparatus since it relates to UV intensity and dose. In general, the parameter/s associated with the transmittance of an optical filter may be ultraviolet light dose or ultraviolet light intensity. The same parameters may be monitored for the operation of a discharge lamp, but pulse count may additionally or alternatively be monitored since discharge lamps are generally warrantied for a specific number of pulses. In any case, when a sensor system is to be used to monitor parameter/s associated with both the operation of a discharge lamp and the transmittance of an optical filter, the sensor system may be configured to monitor the same parameters or different parameters regarding the two components. In some embodiments, a sensor system may include a single sensor configured to measure parameter/s associated with a discharge lamp and an optical filter. In other embodiments, however, a sensor system may include distinct sensors for measuring respective parameters of a discharge lamp and an optical filter.

An exemplary sensor system for apparatus 20 of FIG. 1 includes sensor 72 arranged on the underside of reflector system 60 and sensor 74 arranged in the encasement comprising discharge lamp 22. In general, sensor 74 may be used to monitor a parameter associated with the operation of discharge lamp 22 and, more specifically, may be used to monitor light emitted from discharge lamp 22 prior to passing through optical filter 40. FIG. 1 illustrates sensor 74 disposed on a sidewall surface of cup portion 42, but sensor 74 may be arranged at any location within the encasement of discharge lamp 22. In other embodiments, sensor 74 may be omitted from apparatus 20. In particular, sensor 72 may, in some embodiments, be configured to monitor parameters associated with the operation of discharge lamp 22 (such as by pulse count) and, thus, sensor 74 may not be needed. In any case, sensor 72 may be used to monitor a parameter associated with the transmittance of optical filter 40 and, thus, may be arranged at any location on apparatus 20 or nearby apparatus 20 to receive light passed through optical filter 40. FIG. 1 shows sensor 72 arranged on the underside of reflector system 60, but such a placement is exemplary.

As noted above, it may be advantageous, in some cases, to be able to arrange an optical filter in and out of alignment with a discharge lamp, depending on the desired operation of an apparatus. Example embodiments include those in which an apparatus will be used in various rooms, some with windows and others with no windows. As noted above, it may be advantageous to have an optical filter arranged in alignment with a discharge lamp in rooms having windows. In contrast, however, it may be beneficial to be able to arrange an optical filter out of alignment with a discharge lamp in a closed room with no windows to prevent unnecessary degradation of the optical filter. More specifically, since the visible light generated by a discharge lamp in a closed room will not be seen, filtering the light may not be needed. Furthermore, as noted above, the ability of an optical filter to transmit ultraviolet radiation will decrease in relation to its time of exposure to UV radiation due to solarization. As such, having the ability to arrange an optical filter out of alignment with a discharge lamp may offer a manner in which to extend the life of an optical filter for a given apparatus.

Exemplary variations of apparatus 20 which are configured such that an optical filter may be arranged in and out of alignment with discharge lamp 22 are shown in FIGS. 2a-2c. In particular, FIGS. 2a-2c illustrate variations to the placement of optical filter 40 relative to its placement in FIG. 1 as being part of the encasement of discharge lamp 22. It is noted that FIGS. 2a-2c merely set forth examples of configurations for accommodating an optical filter in and out of alignment with a discharge lamp, but such exemplary disclosures and depictions should not be construed to limit the configurations of apparatuses described herein for such an objective. It is further noted that although FIGS. 2a-2c are described as variations to apparatus 20 in FIG. 1, FIGS. 2a-2c only depict a fraction of an apparatus in the interest to simplify the drawings. In particular, FIGS. 2a-2c only depict the placement of optical filter 40 relative to the encasement of discharge lamp 22 within support structure 24. It is noted that features depicted in FIGS. 2a-2c with the same configurations as described in reference to FIG. 1 (i.e., discharge lamp 22, support structure 24, optical filter 40 and cup portion 42) are denoted with the same reference numbers and the descriptions of such features are not reiterated for the sake of brevity. Since the embodiments of FIGS. 2a-2c do not have optical filter 40 as part of the encasement of discharge lamp 22, each of FIGS. 2a-2c include a new feature relative to FIG. 1, specifically encasement topper 82. In general, encasement topper 82 may be of an optically transparent material, such as but not limited to quartz.

As shown in FIG. 2a, variation 80 to apparatus 20 may include optical filter 40 arranged upon encasement topper 82. In such a configuration, optical filter 40 may, in some embodiments, simply be placed on top of support structure 24 (i.e., the portion of support structure 24 comprising encasement topper 82) without a means of securing optical filter 40 to the support structure. Alternatively, variation 80 may include a means to affix optical filter 40 to support structure 24. In either case, placement of optical filter 40 upon encasement topper 82 may be manual or may be automated. FIG. 2b illustrates variation 84 of apparatus 20 slightly modified relative to variation 80 in FIG. 2a. In particular, FIG. 2b illustrates the inclusion of hinge 86 mounted to one side of optical filter 40. In this manner, optical filter 40 may be arranged upon encasement topper 82 and may be removed from such a position without detachment from the apparatus. Hinge 86 may be configured to pivot optical filter 40 any angle between 90 and 180 degrees relative to the position of optical filter 40 shown in FIG. 2b. Thus, optical filter 40 may be put in any position between an upright position and a position on support structure 24 opposing discharge lamp 22 when moved from the position above the discharge lamp. Movement of optical filter 40 in such embodiments may be manual or may be automated. A different variation of apparatus 20 is depicted in FIG. 2c which has optical filter 40 arranged upon a slider for moving the optical filter in and out of alignment with discharge lamp 22 along the upper surface of support structure 24, as is indicated by the horizontal double arrow. The movement of optical filter 40 on the slider may be manual or automated.

Regardless of the configuration of apparatus 20 such that optical filter 40 may be arranged in and out of alignment with discharge lamp 22, apparatus 20 may be configured such that optical filter 40 is protected from exposure to ultraviolet light when not in alignment with discharge lamp 22. For instance, apparatus 20 may, in some embodiments, include a compartment in which optical filter 40 may be placed when it is removed from and/or repositioned in the apparatus. In addition or alternatively, apparatus 20 may include a component to cover optical filter 40 when it is taken out of alignment with discharge lamp 22. In any case, as set forth above, each of the embodiments disclosed in FIGS. 2a-2c may be automated and, thus, not only may the ultraviolet discharge lamp apparatuses disclosed herein be configured to accommodate an optical filter in and out of alignment with a discharge lamp, the apparatuses may, in some embodiments, include a means for automatically moving the optical filter in and out of alignment with the discharge lamp. Such a means may include any mechanism/s known in the art for moving objects. In some embodiments, the determination of whether to move the optical filter and/or the timing to move the optical filter may be determined by a user of apparatus 20. In other cases, however, apparatus 20 may include program instructions which are executable by CPU 32 such that the determination of whether to move the optical filter and/or the timing to move the optical filter may be automated.

As noted above, it may be advantageous, in some embodiments, to access and/or analyze the characteristics of a room and use such information to determine a number of operational parameters for apparatus 20. In particular, it may be advantageous to determine whether there is a window in the room in which apparatus 20 is arranged and determine a position of optical filter 40 based on the data. In this manner, in embodiments in which a window is detected in a room in which apparatus 20 is arranged, optical filter 40 may be arranged in alignment with discharge lamp 22 prior to operating the discharge lamp to produce light. Conversely, in embodiments in which a window is not detected in a room in which apparatus 20 is arranged, optical filter 40 may be arranged out of alignment with discharge lamp 22 prior to operating the discharge lamp to produce light. It is noted that the optional configurations to affect movement of optical filter 40 may be in addition or alternative to the configurations noted above for affecting movement of reflector 62. As noted above, apparatus 20 may include or may be configured to access a database listing characteristics of one or more rooms and/or apparatus 20 may include system 70, for collecting and/or generating data regarding characteristics of a room. In general, any system known in the art for determining whether there is a window in the room may be used for system 70 in such cases, such as but not limited to reflection sensors. As further described above, CPU 32 of apparatus 20 may be configured to retrieve and/or access the data, determine a position of optical filter 40 based on the data, and either relay the determined position to user interface 34 and/or send a command in accordance with the determined position to a means within apparatus 20 for automatically moving optical filter 40.

FIG. 2c illustrates an optional feature for apparatus 20 in conjunction with including a slider for optical filter 40, specifically the inclusion of thermal rejuvenation chamber 90 adjacent to support structure 24. As noted above, the ability of an optical filter to transmit ultraviolet radiation will decrease in relation to its time of exposure to UV radiation due to solarization. In some cases, however, the solarization effects may be reversed if the optical filter is heated at high temperatures, such as on the order of 500° C. Although such a process may be done independent of apparatus 20, it may be advantageous in some embodiments to incorporate the process into apparatus 20 to reduce downtime of the apparatus and/or such that a replacement optical filter does not need to be on hand while optical filter 40 is being rejuvenated. Due to the high temperatures required to reverse the effects of solarization, it is preferable that thermal rejuvenation chamber 90 be a distinct chamber from support structure 24. In addition, it would be advantageous for thermal rejuvenation chamber 90 to be configured to not only withstand, but substantially contain the heat generated therein to prevent heat degradation/damage of components within support structure 24.

As shown by the downward arrow in FIG. 2c, apparatus 20 may, in some embodiments, be configured to move optical filter 40 into thermal rejuvenation chamber 90. In other embodiments, it may be done manually. In either case, the movement of optical filter 40 into thermal rejuvenation chamber 90 may, in some embodiments, be dependent on measurements taken regarding the transmittance of optical filter 40. In particular, information collected from sensor 72 regarding the transmittance of optical filter 40 may be used to determine when to move the optical filter into thermal rejuvenation chamber 90. Although the inclusion of a thermal rejuvenation chamber may be beneficial in some apparatuses, it is not a requirement and, thus, may be omitted in some embodiments. Furthermore, the features of thermal rejuvenation chamber 90 and optical filter 40 being on a slider as shown in FIG. 2c are neither mutually exclusive nor mutually inclusive for an apparatus and, thus, an apparatus may include one or both features. In fact, any of the apparatuses described herein which include an optical filter may include a thermal rejuvenation chamber, including those described above in reference to FIGS. 1, 2a and 2b as well as those described below in reference to FIGS. 3-8.

As noted above, the ultraviolet discharge lamp apparatuses described herein are not restricted to embodiments in which a discharge lamp is disposed (i.e., nested) within the confines of a support structure as depicted in FIG. 1. Rather, ultraviolet discharge lamp apparatuses may alternatively have a discharge lamp which is arranged at least partially exterior to a support structure. An exemplary embodiment of a variation to apparatus 20 in which discharge lamp 22 is arranged exterior to support structure 24 is shown in FIG. 3. As shown in FIG. 3, variation 92 may include a different optical filter configuration than that shown for apparatus 20 in FIG. 1, specifically optical filter 94 instead of optical filter 40. In addition to being configured to attenuate visible light propagated above discharge lamp 22, optical filter 94 is configured to attenuate visible light propagated sideways from discharge lamp to account for discharge lamp 22 being arranged above support structure 24. Due to such a displacement of discharge lamp 22, cup portion 42 may, in some embodiments, be omitted from support structure 24 as shown in FIG. 3. In such cases, variation 92 may, in some embodiments as shown in FIG. 3, include reflective plane 96 disposed below discharge lamp 22 to redirect light emitted from the bottom of discharge lamp 22 upward.

As further noted above, the ultraviolet discharge lamp apparatuses described herein are not restricted to embodiments in which a discharge lamp is arranged in a "horizontal position." Rather, the ultraviolet discharge lamp apparatuses described herein may include discharge lamps arranged at any angle relative to the surface plane at which the lamp is supported. Examples of ultraviolet discharge lamp apparatuses having discharge lamps arranged in a "vertical position" (i.e., arranged lengthwise perpendicular to a plane of the apparatus at which the lamp is supported) are shown in FIGS. 4-8. Each of such embodiments include a support structure, a power circuit, trigger circuit and accompanying optional components (e.g., CPU, user interface, sensors, room characteristics system, hinge, slider, and/or thermal rejuvenation chamber) as described for FIG. 1. Each of such features, however, has not been depicted in each of FIGS. 4-8 for simplicity purposes as well as to emphasize the differing configurations of the depicted optical filters and reflector systems. Furthermore, each of such features has not been described in reference to FIGS. 4-8 for the sake of brevity.

Turning to FIG. 4, apparatus 100 is shown having a discharge lamp assembly supported above support structure 102 and arranged lengthwise perpendicular to a plane of support structure 102. The discharge lamp assembly includes discharge lamp 104 surrounded by optical filter 106 and vertically disposed between fan 108 and ozone filter 119. In addition, the discharge lamp assembly includes base 110 and air filter 112 supported at base 114. Optical filter 106 may, in some embodiments, be a wall of an encasement enclosing discharge lamp 104, making up a forced air cooling system for apparatus 100 with fan 108. Apparatus 100 further includes reflector 118 affixed to ozone filter 119 at the top of optical filter 106. The characteristics of reflector 118, discharge lamp 104 and the cooling system of apparatus 100 as well as the optical characteristics of optical filter 106 may generally include those described above for all of the ultraviolet discharge lamp apparatuses considered herein and are not reiterated for the sake of brevity. As with the embodiments described above, several of the components included in apparatus 100 may be replaced and/or omitted for other configurations of ultraviolet discharge lamp apparatuses described herein, particularly optical filter 106, reflector 118, ozone filter 119 and the cooling system of apparatus 100. As such, the compilation and configurations of components depicted in FIG. 4 are not necessarily mutually inclusive.

Furthermore, it is noted that apparatus 100 may include additional components (i.e., components other than what is depicted in FIG. 4). For example, in some embodiments, apparatus 100 may include an optically transparent intermediate barrier arranged between and spaced apart from discharge lamp 104 and optical filter 106. An exemplary material for the intermediate barrier may be quartz, but its composition is not so limited. The intermediate barrier may be a wall of an encasement enclosing discharge lamp 104 and, thus, may be vertically disposed between fan 108 and ozone filter 119 and part of the cooling system for apparatus 100. In such cases, optical filter 106 surrounds the intermediate barrier as a distinct glass piece spaced apart from the intermediate barrier and is secured to base 110, fan 108, and/or reflector 118. Incorporating an intermediate barrier between discharge lamp 104 and optical filter 106 may be advantageous when it is desirable to have the capability to arrange optical filter 106 in and out of alignment with discharge lamp 104 or when it is desirable to have optical filter 106 move independent of discharge lamp 104 during operation of the apparatus. In particular, an intermediate barrier may take on the role as being part of an encasement to discharge lamp 104, allowing movement of optical filter 106 without sacrificing a cooling system for discharge lamp 104.

As set forth in more detail below, it may be advantageous in some embodiments to move an optical filter of the apparatuses described herein about a central axis (e.g., to rotate or oscillate) during the operation of an apparatus. It is generally not desirable, however, to move a discharge lamp in the same manner due to concerns of damage to the discharge lamp. Thus, in some embodiments, optical filter 106 may be secured to base 110 or fan 108, but may be spaced apart from reflector 118 or vice versa. In such cases, apparatus 100 may include an additional component/s coupled to optical filter 106 which is configured to block light, particularly visible light, in the gap between optical filter 106 and base 110, fan 108 or reflector 118. Exemplary components which may be particularly suitable for such function may be a dense collection of bristles.

In any case, although the amount and rate of cooling gas discharged from an apparatus may vary greatly and may generally depend on the design specifications of the apparatus, in some embodiments the amount and rate of gas may be sufficient to trigger sprinkler systems in a room, particularly when the outlet duct of a cooling system is directed toward the ceiling as was discovered during the development of the apparatuses described herein. As such, in some cases, apparatus 100 may include a cap component spaced above the discharge lamp assembly to allow for air discharge to the side of the apparatus rather than above the apparatus. An exemplary configuration of a cap component is shown in FIG. 5 and described in more detail below. An alternative solution to prevent sprinkler systems from being triggered from exhaust of a cooling system is to lower the flow rate of gas through the lamp assembly if doing so does not cause the discharge lamp to be above its suggested maximum operating temperature. On the contrary, decreasing the gas flow rate may not be desirable in some cases (i.e., even if it does not cause the discharge lamp to exceed is maximum operating temperature) since operating discharge lamps at cooler temperatures generally offers a longer life for the lamp and theoretically generates more ultraviolet light.

FIG. 5 illustrates variation 115 to apparatus 100 having cap component 117 arranged above the lamp discharge assembly of the apparatus and, more specifically, above an outlet of the cooling system within the lamp discharge assembly such that exhaust therefrom may be directed sideways rather than above the apparatus. As shown in FIG. 5, cap component 117 may be domed to prevent objects from being placed thereon. Such a dome configuration is not restricted to embodiments in which an apparatus includes a cap component above a discharge lamp assembly. In particular, the top of a discharge lamp assembly may be domed in some cases to prevent objects from being placed thereon. Furthermore, the inclusion of cap component 117 is not mutually inclusive to embodiments in which ozone filter 119 comprises the entire top portion of the discharge lamp assembly as shown in FIG. 5. In particular, any of the apparatuses disclosed herein may include a component spaced apart from an outlet of its cooling system to direct exhaust therefrom.

As shown in FIG. 4, apparatus 100 may, in some embodiments, include linear actuators 116 coupled to base 114. In general, linear actuators 116 may be used to move the discharge lamp assembly and attached reflector 118 in and out of support structure 102. Such a configuration may be advantageous for protecting the discharge lamp assembly and the attached reflector from damage while apparatus 100 is not in use and, particularly, in transport. In other embodiments, linear actuators 116 may be used to move the discharge lamp assembly and the attached reflector while apparatus 100 is in operation and, in some cases, while discharge lamp 104 is emitting light. In particular, in some embodiments, it may be advantageous to move the discharge lamp assembly and the attached reflector while apparatus 100 is in operation to aid in the distribution of ultraviolet light within a room in which the apparatus is arranged. Other manners of effecting movement of the discharge lamp assembly and attached reflector may be used and, thus, the apparatuses considered herein are not necessarily limited to linear actuators 116 to achieve such an objective. For example, apparatus 100 may alternatively have fixed rails along which the discharge lamp assembly and attached reflector may move. In any case, the configuration to move a discharge lamp assembly during operation of an apparatus is not exclusive to embodiments in which the apparatus includes a reflector attached to and/or above the discharge lamp assembly.

Since apparatus 100 is configured to extend discharge lamp 104 beyond an exterior surface of support structure 102, optical filter 106 is configured to surround discharge lamp 104 and, thus, may be cylindrical in shape in some cases as shown in FIG. 4. Such a configuration of optical filter 106 may include a right circular cylindrically formed optical filter glass or may include a film having the desired optical characteristics disposed upon an optically transparent right circular cylindrical substrate, such as quartz for example. Other configurations of optical filters which surround discharge lamp 104 may also be possible as described in more detail below in reference to FIGS. 6 and 7. In yet other cases, optical filter 106 may be omitted from apparatus 100. In particular, as noted above although the inclusion of an optical filter may be beneficial in some of the apparatuses described herein, it is not necessarily a requirement.

A benefit of having apparatus 100 configured to extend discharge lamp 104 beyond an exterior surface of support structure 102 is that ultraviolet light emitted from discharge lamp 104 and, if applicable, passing through optical filter 106 encircles an exterior surface of the apparatus without necessarily the inclusion of reflector 118. In particular, the extension of discharge lamp 104 beyond an exterior surface of support structure 102 innately causes ultraviolet light emitted from discharge lamp 104 and, if applicable, passing through optical filter 106 to encircle the lamp housing, which comprises an exterior surface of the apparatus. Depending on the height of support structure 102 as well as the height of the discharge lamp assembly, the extension of discharge lamp 104 beyond an exterior surface of support structure 102 may cause ultraviolet light emitted from discharge lamp 104 to encircle support structure 102 as well. Further yet, the extension of discharge lamp 104 beyond an exterior surface of support structure 102 may, in some embodiments, cause ultraviolet light to propagate to a region which is between approximately 2 feet and approximately 4 feet from a floor in which apparatus 100 is arranged, which as described above may be considered a high touch zone in a room needing particularly effective disinfection. In yet other cases, although the suspension of discharge lamp 104 above support structure 102 may be beneficial for distributing light around apparatus 100, the placement of discharge lamp 104 is not necessarily so limited. In particular, discharge lamp 104 may alternatively be arranged upon support structure 102 or may be partially disposed with support structure 102.

Since extending a discharge lamp beyond an exterior surface of a support structure is effective for propagating light around an apparatus, a reflector system for redirecting ultraviolet light propagating away from the apparatus may not be needed in some embodiments of the apparatuses described herein, particularly for apparatuses having vertically positioned discharge lamps. In some cases, however, such a reflector system may be included as shown in apparatus 100 of FIG. 4. As noted above, a reflector system of apparatus 100 may include reflector 118 affixed to ozone filter 119 at the top of optical filter 106. Although such a configuration may be advantageous for moving reflector 118 with the discharge lamp assembly (i.e., in a vertical direction in and out of support structure 102), the configuration of the apparatus is not so limited. In particular, reflector 118 may alternatively be detached from the discharge lamp assembly in apparatus 100. Such a configuration may be advantageous in embodiments in which it is desirable to move the reflector independent of the discharge lamp assembly, such as for optimizing a redirection of ultraviolet light to a specific area. Other alternative configurations for apparatus 100 include reflector 118 and ozone filter 119 having the same or similar diameter and being vertically disposed relative to each other as shown in FIG. 5. In particular, FIG. 5 illustrates variation 115 to apparatus 100 in which ozone filter 119 comprises a top portion of the discharge lamp assembly with reflector 118 comprising the bottom portion of the assembly. Such a configuration may advantageously allow greater air flow through the lamp housing and, thus, provide a more efficient cooling system. In yet other embodiments, ozone filter 119 may be omitted from apparatus 100 and replaced with an air filter and/or an optical filter.

In any case, reflector 118 may be circular as shown in FIG. 4 and, may be specifically conical in some embodiments. Other shapes, however, may be considered for reflector 118. In some embodiments, reflector 118 may include holes such that some ultraviolet light may be propagated above apparatus 100. In any case, apparatus 100 may, in some embodiments, include additional reflector/s for redirecting ultraviolet light propagating from either discharge lamp 104 and/or reflector 118. For instance, in some embodiments, apparatus 100 may include a reflector disposed around the base of discharge lamp assembly. In some cases, the additional reflector may be attached to the discharge lamp assembly such that it moves with it. In other embodiments, the additional reflector may be affixed to the upper surface of support structure 102 and the discharge lamp assembly may move through it. As with the shape of reflector 118, the additional reflector may, in some cases, be circular and even conical, but other shapes may be considered. Regardless of the configuration of reflector 118 or even its inclusion within apparatus 100, the base to which discharge lamp 104 is supported (e.g., the top of fan 108) may include a reflector.

As noted above, other configurations of optical filters which surround discharge lamp 104 may be considered for the ultraviolet discharge lamp apparatuses disclosed herein and are shown in FIGS. 6 and 7. It is noted that the variations of apparatuses illustrated FIGS. 6 and 7 are used to emphasize different configurations of optical filters which may be considered for the apparatuses described herein. Although not shown, the variations of apparatuses illustrated in FIGS. 6 and 7 may include any of the components shown and described in FIGS. 1-5. For example, the variations may include any components of the lamp assembly described in reference to FIG. 4 as well as reflector 118. Furthermore, the size of ozone filter 119 in FIGS. 6 and 7 may be altered from its depiction and/or ozone filter 119 may be omitted from the configurations of FIGS. 6 and 7, depending on the design specifications of an apparatus.

FIG. 6 illustrates variation 120 to apparatus 100 having multifaceted optical filter 122 surrounding discharge lamp 104. FIG. 6 illustrates multifaceted optical filter 122 arranged upon support structure 102, but such an arrangement is exemplary. Multifaceted optical filter 122 may alternatively be suspended above support structure 102 as is shown and depicted for optical filter 106 in FIG. 4. In yet other embodiments, multifaceted optical filter 122 and accompanying discharge bulb 104 may be partially disposed within support structure 102. In any case, a multifaceted optical filter generally includes multiple panels of optical filters fused together. Although multifaceted optical filter 122 is shown including six panels, it is not so limited. In particular, the multifaceted optical filters considered for the apparatuses described herein may include any plurality of optical filter panels. In addition, the optical filter panels may be made of optical filter glass material or may be made of optically transparent substrates, such as quartz for example, having films with the desired optical characteristics disposed thereon. In either case, the optical filter panels may, in some embodiments, include narrow strips of a different material (such as metal or plastic) for structural support. In some cases, one or more of the narrow support strips may partially or entirely include a reflective material to aid in redirection of light emitted from the discharge lamp around which they are arranged.

In some embodiments, a multifaceted optical filter may be cheaper than a right circular cylindrical optical filter, particularly for embodiments in which the optical filter is made of an optical filter glass material. A disadvantage of employing a multifaceted optical filter, however, may be that ultraviolet light may be blocked where the plates are fused and/or where support strips are disposed and, thus, areas of a room in which the apparatus is arranged may not be adequately disinfected. One way to overcome such deficiency is to move the multifaceted optical filter during operation of the apparatus. In particular, the multifaceted optical filter may be moved around a central axis such that ultraviolet light propagated to a region encircling apparatus 100 during the operation of the apparatus may collectively occupy the entirety of the encircling region. The multifaceted optical filter may be rotated a full revolution or more during the operation of the apparatus or may be rotated less than a revolution during the operation of an apparatus. In some embodiments, the multifaceted optical filter may be moved a fraction of a revolution, wherein the fraction corresponds to the number of optical panels comprising the multifaceted optical filter. For example, in embodiments in which the multifaceted optical filter includes six optical panels, the multifaceted optical filter may be moved ⅙ of a revolution.

In any case, some of the apparatuses described herein may include a means for moving an optical filter around a central axis. Such a means may include any mechanism known in the art for moving an object and, in further embodiments, may also include program instructions which are executable by CPU 32 such that the timing to move the optical filter around a central axis may be automated. As noted above, although it may be advantageous in some embodiments to move an optical filter of the ultraviolet discharge lamp apparatuses described herein about a central axis during the operation of an apparatus, it is generally not desirable to move a discharge lamp in the same manner due to concerns of damaging the discharge lamp. Thus, in some embodiments, variation 120 may include an intermediate barrier between discharge lamp 104 and multifaceted optical filter 122. As described above, the intermediate barrier may be part of an encasement around discharge lamp 104. In addition, multifaceted optical filter 122 may be configured to move independent of the intermediate barrier.

In yet other embodiments, multifaceted optical filter 122 may not be configured to move about a central axis during the operation of an apparatus. In particular, it is theorized that light propagated from neighboring optical filter panels of multifaceted optical filter 122 may converge at some point and, thus, ultraviolet light may encircle an exterior surface of apparatus 100 without moving multifaceted optical filter 122 around a central axis during operation of apparatus 100. In yet other embodiments, discharge lamp 104 may include a configuration which counteracts potential blocking from the fused areas of the optical filter panels and/or support strips disposed on multifaceted optical filter 122. For example, discharge lamp 104 may include a U-shaped bulb having a spacing between the "bars" of the U that is larger than the width of the fused areas and/or the support strips. In either of such cases, apparatus 100 may be referred to as being configured such that at least some of the ultraviolet light emitted from discharge lamp 104 and passed through multifaceted optical filter 122 encircles an exterior surface of the apparatus. Alternatively, it may be determined that the gaps of coverage incurred by the fused areas of the optical filter panels and/or where support strips are disposed on multifaceted optical filter 122 may not be significant and, thus, movement of multifaceted optical filter 122 may not be needed.

FIG. 7 illustrates yet another configuration of an optical filter which may be used within the apparatuses considered herein. In particular, FIG. 7 illustrates variation 124 to apparatus 100 having an assembly of optical filter 126 and reflector 128 surrounding discharge lamp 104. As shown in FIG. 7, optical filter 126 and reflector 128 may, in some embodiments, be of approximately equal size along the cylindrical sidewalls of the assembly. However, other configurations are possible, including those in which optical filter 126 is larger than the portion of reflector 128 along the sidewalls of the assembly and those in which optical filter 126 is smaller than the portion of reflector 128 along the sidewalls of the assembly. As such, a more general description of an optical filter/reflector assembly which may be considered for the apparatuses described herein may be an assembly which includes an optical filter and a reflector opposing the optical filter or vice versa.

As shown in FIG. 7, reflector 128 may, in some cases, further comprise a top portion of the assembly. Other configurations for the assembly top, however, may be considered, including optical filter 126 alternatively comprising the top portion of the assembly or having a combination of reflector 128 and optical filter 126 comprising the top portion of the assembly. It is further noted that the shape of the optical filter/reflector assembly is not restricted to being a right circular cylinder as shown in FIG. 7. Rather, one or more of reflector 128 and optical filter 126 may include multiple panels and, thus, the assembly may be of a polygonal cylinder shape in some cases. In addition or alternatively, the top of the assembly may be slanted or, more generally, have a variation in height. Such a configuration may be particularly advantageous when at least a portion of the top includes reflector 128 such that ultraviolet light may be redirected downward to a desirable region within a room. In addition or alternatively, such a configuration may be advantageous for preventing exhaust from a cooling system of the apparatus from being directly routed to a ceiling of the room in which the apparatus is arranged.

In any case, the optical filter/reflector assembly of FIG. 7 may be effective for targeting a specific area within a room which is adjacent to the apparatus, such as an area having a high concentration of objects. In some embodiments, the optical filter/reflector assembly may be configured to move. For example, in some cases, the optical filter/reflector assembly may be configured to oscillate. Such a configuration may be advantageous when a given target area is larger than the span to which the optical filter/reflector assembly can effectively emit ultraviolet light when it is stationary. In other embodiments, the optical filter/reflector assembly may be configured to rotate. In any case, the movement of the optical filter/reflector assembly may, in some embodiments, be based on characteristics of a room in which apparatus 100 is arranged. For example, if a relatively high number of objects within a room are in the same general area, it may be beneficial to position the optical filter/reflector assembly to direct light to that specific area as compared to other areas in the room.

Similar to apparatus 20 described in reference to FIGS. 1 and 2*a*-2*c*, apparatus 100 may include or may be configured to access a database listing characteristics of one or more rooms and/or apparatus 100 may include system 70 for collecting and/or generating data regarding characteristics of a room. Any system known in the art for generating, collecting and/or analyzing characteristics of a room may be used. Examples include dosimeters, spatial sensors and/or photo recognition systems. In some cases, apparatus 100 may further include CPU 32 to retrieve data, determine a position of the optical filter/reflector assembly based on the data, and either relay the determined position to user interface 34 and/or send a command in accordance with the determined position to a means within apparatus 100 for automatically moving the optical filter/reflector assembly.

As noted above, the ultraviolet discharge lamp apparatuses described herein may include a lens system to either diverge or converge light propagating away from the discharge lamp. The configuration of a lens system to achieve either objective involves the placement, shape, size and configuration of the lens system. Set forth below are descriptions of example converging lens systems and example diverging lens systems for apparatus 100 depicted in FIG. 4. It is noted converging or diverging lens systems may be similarly configured into apparatus 20 depicted in FIG. 1 or into any germicidal lamp apparatus described herein to achieve a desired redirection of light from a germicidal lamp. In particular, any of the germicidal lamp apparatuses described herein, including those described in reference to FIGS. 1-7, may include a lens system with one or more lenses of any size, shape and configuration and arranged at any position within an apparatus to achieve a desired redirection of light. In addition, any of the germicidal lamp apparatuses described herein may be configured to move lens/es relative to the germicidal lamp of the apparatus and, in some cases, move the lens/es based on characteristics of a room in which an apparatus is arranged.

An example of an ultraviolet discharge lamp apparatus including a lens system is shown in FIG. 8 in which converging lens system 127 is arranged around optical filter 106. In particular, FIG. 8 is a cross-sectional view of a variation 125 of apparatus 100 taken along axis AA shown in FIG. 4. As shown in FIG. 8, converging lens system 127 encircles optical filter 106 and discharge lamp 104 and, thus, converges light to an area which encircles apparatus 100. In some cases, converging lens system 127 may be a single continuous component as shown in FIG. 8 (i.e., converging lens system 127 may be a simple or complex optical element of continuous construction around optical filter 106). In other embodiments, converging lens system 127 may be multifaceted around optical filter 106 similar to the configuration described for multifaceted optical filter 122 in reference to FIG. 6. In other words, converging lens system 127 may be made of multiple converging lens (simple or complex) fused together in a cylindrical arrangement. In such cases or in any embodiments in which multiple lens are employed, it may, in some cases, be advantageous for apparatus 100 to include a means for collectively moving the converging lenses about a central axis (e.g., oscillate or rotate at least partially) during the operation of apparatus 100 such that the converged light from each lens may be distributed across a region of a room. In some cases, apparatus 100 may include a converging lens system which does not encircle optical filter 106 and discharge lamp 104. As noted above, the term "encircle" as used herein refers to the formation of a continuous circle around an object. In some cases, apparatus 100 may include a single non-encircling lens (simple or complex) arranged adjacent to optical filter 106. In other embodiments, apparatus 100 may include multiple converging lenses spaced apart from each other adjacent to optical filter 106 and, in some cases, surrounding optical filter 106.

In any of such embodiments, apparatus 100 may, in some cases, be configured such that the convergence of light from the lens/es may be changed. For instance, apparatus 100 may be configured to reposition (i.e., axially drive) one or more converging lens/es toward and/or away from optical filter 106, or more specifically discharge lamp 104, to change the convergence of light from the lens/es. To accommodate such a configuration, apparatus 100 may include a means for driving and securing the one or more repositionable lens at different positions within apparatus 100 and various configurations of such a means may be considered. In addition or alternatively, in cases in which a converging lens system includes a complex lens, apparatus 100 may, in some embodiments, be configured to add or remove lens/es to the complex lens to change the convergence of light from the lens/es. To accommodate such a configuration, apparatus may include a means by which to access and move the applicable lens/es in and out of alignment with the complex lens and possibly a means by which to store them. Other manners and/or configurations for apparatus 100 may be considered for allowing the convergence of light from lens/es to be changed.

In some cases, a repositionable lens may be moved manually within apparatus 100. In other embodiments, however, apparatus 100 may include a means for moving a repositionable lens. In further of such cases, apparatus 100 may, in some embodiments, be configured to move a repositionable lens continuously or periodically while apparatus 100 is in operation. In particular, apparatus 100 may be programmed to move a repositionable lens while apparatus 100 is in operation according to a schedule of positions or in response to UV reflection measurements received by the apparatus during operation of the apparatus. The reference of apparatus 100 being in operation refers to periods when the components of the apparatus have been activated to operate discharge lamp 104 and specifically the operations by which to generate a radiating plasma within the discharge lamp. As noted above, discharge lamp 104 may, in some embodiments, be configured to generate continuous light once the lamp is triggered and, as such, the reference of apparatus 104 being in operation in such cases refers to the time used to trigger the lamp as well as the time of continuous light emission. In other embodiments, a flashlamp or a pulsed light source may be used for discharge lamp 104 and, in such cases, the reference of apparatus 100 being in operation refers to the times in which light is emitted from the lamp as well as times in between the light flashing.

In some embodiments, positioning repositionable lens/es a particular distance from discharge lamp 104 may be based on characteristics of a room in which apparatus 100 is arranged. For example, if a specific area or object within a room is specifically targeted for disinfection, it may be beneficial to position a converging lens to direct more light to that area or object based on the distance the region or object is from apparatus 100. Through the operational coupling of system 70 to CPU 32, CPU 32 may be configured to retrieve distance measurements from system 70, determine position/s of the converging lens/es based on the measurements (via a database table or an algorithm) and either relay the position/s to user interface 34 and/or send a command in accordance with the position/s to a means within apparatus 20 for moving the converging lens/es.

In any of the aforementioned cases, the converging lens/es may be of any size, shape and configuration and may be arranged at any position within an apparatus to achieve the desired redirection of light. In addition, the converging lens/es may be simple or complex lens/es. As such, the depiction of converging lens system 127 in FIG. 8 should not limit the scope of configurations which may be considered for a converging lens. For example, in some embodiments, converging lens system 127 may abut the bottom portion of reflector 118 such that the gap depicted in FIG. 8 between the components is omitted. Such a configuration may be advantageous for converging nearly all of the light emitted from discharge lamp 104 (i.e., with the exception of the nominal light which may be absorbed into fan 108 and ozone filter 119). In yet other cases, converging lens system 127 may be arranged exterior to the canopy of reflector 118. Other configurations may be considered as well. For instance, converging lens system 127 may be smaller than discharge lamp 104 in some embodiments. In addition or alternatively, lens/es of converging lens system 127 may be arranged at a nonparallel angle relative to discharge lamp 104. Yet another optional configuration is that apparatus 100 may additionally or alternatively include one or more converging lens/es in the space between discharge lamp 104 and optical filter 106 arranged in any of the configurations noted above.

In some cases, a converging lens system for apparatus 100 may be configured to converge light from discharge lamp 104 to a region between approximately 2 feet and approximately 4 feet from a floor of a room in which apparatus 100 is arranged. As noted above, such a region is considered a "high touch" region of a room since objects of frequent use are generally placed in such a space. The configuration of a converging lens system to converge light to a region between approximately 2 feet and approximately 4 feet from a floor of a room may generally depend on the size and shape of the lens/es relative to the size and shape of the discharge lamp and relative to the distance the discharge lamp is from the floor and/or the ceiling of the room. Furthermore, the configuration of a converging lens system to converge light to a region between approximately 2 feet and approximately 4 feet from a floor of a room may generally depend on the distance the lens/es are from discharge lamp. One skilled in the art would be apprised of how to take such parameters into consideration for developing a lens system to converge light from discharge lamp 104 to a region between approximately 2 feet and approximately 4 feet from a floor of a room in which apparatus 100 is arranged.

As noted above, an apparatus described herein may include a lens system configured to diverge light propagating away from the discharge lamp to increase the size of an area exposed to ultraviolet light by the apparatus. Thus, in some embodiments, apparatus 100 may include a diverging lens system exterior to optical filter 106 or between optical filter 106 and discharge lamp 104. In general, the diverging lens/es of the diverging lens system may be of any size and shape and may be arranged at any position within an apparatus to achieve the desired redirection of light. In addition, the diverging lens/es may be simple or complex lens/es. In some cases, the diverging lens system may include configurations similar to those described above in reference to converging lens system 127. In particular, the diverging lens system may include a single continuous diverging lens surrounding discharge lamp 104, a single diverging lens which does not encompass discharge lamp 104, a multifaceted diverging lens system, or multiple diverging lenses spaced apart from each other.

Furthermore, in cases in which the diverging lens system includes multiples lenses, apparatus 100 may, in some cases, be configured to collectively move the diverging lenses about a central axis (e.g., oscillate or rotate at least partially) during the operation of apparatus 100 such that the diverged light from each lens may be distributed across a region of a room. Moreover, apparatus 100 may, in some cases, be configured such that the divergence of light from the lens/es may be changed. For example, in cases in which a complex diverging lens system is used, apparatus 100 may, in some embodiments, be configured to add or remove lens/es to the complex lens to change the divergence of light from the lens/es. In addition or alternatively, apparatus 100 may be configured to reposition one or more of the diverging lens/es toward or away from discharge lamp 104 to change the divergence of the light from the lens/es. Other manners and/or configurations for apparatus 100 may be considered for allowing the divergence of light from lens/es to be changed. Repositioning the diverging lens/es may, in some embodiments, be based on characteristics of a room in which apparatus 100 is arranged. For example, if a relatively large area or object within a room is specifically targeted for disinfection, it may be beneficial to position a diverging lens to expose more of the area or object to the light generated by the discharge lamp. The positioning of the diverging lens in such cases may be based on the distance the region or object is from apparatus 100 as well as the size of the region or object.

Regardless of whether a diverging lens system is configured to move within apparatus 100, a diverging lens system for apparatus 100 may, in some embodiments, be configured to diverge light from discharge lamp 104 to a region between approximately 2 feet and approximately 4 feet from a floor of a room in which apparatus 100 is arranged. Similar to a converging lens system, the configuration of a diverging lens system to diverge light to a region between approximately 2 feet and approximately 4 feet from a floor of a room may generally depend on the size and shape of the lens/es relative to the size and shape of the discharge lamp and relative to the distance the discharge lamp is from the floor and/or the ceiling of the room. Furthermore, the configuration of a diverging lens system to diverge light to a region between approximately 2 feet and approximately 4 feet from a floor of a room may generally depend on the distance the lens/es are from discharge lamp. One skilled in the art would be apprised of how to take such parameters into consideration for developing a lens system to diverge light from discharge lamp 104 to a region between approximately 2 feet and approximately 4 feet from a floor of a room in which apparatus 100 is arranged.

In addition or alternative to the features described above, the ultraviolet discharge lamp apparatuses described herein may, in some embodiments, include multiple discharge lamps. Such apparatuses may include optical filters and/or reflection systems for each discharge lamp in accordance with the descriptions of such features provided above. In some embodiments, an apparatus may include a discharge lamp with an optical filter configured to attenuate a majority amount of visible light emitted therefrom and further include a discharge lamp without an optical filter arranged in its proximity. Such a configuration may be advantageous for alternating the use of the discharge lamps depending on whether it is desired to attenuate visible light during operation of the apparatus. In some cases, some or all of the multiple discharge lamps may be operated by the same power circuit and/or the same trigger circuit. In other embodiments, an apparatus may include a distinct power circuit and/or a distinct trigger circuit for each discharge lamp. In either case, it is contemplated herein that multiple apparatuses each having one or more discharge lamps may be configured to work in communication with each other (i.e., make up a system) to disinfect a room. FIG. 9 illustrates an exemplary system 130 including multiple ultraviolet discharge lamp apparatuses 132 and 142 respectively including discharge lamp assemblies 134 and 144 and sensors 136 and 146. The dotted line between apparatuses 132 and 142 indicates that the units may be configured to communicate with each other and/or may be connected via a central processing unit.

In any case, an apparatus having multiple discharge lamps or a system having multiple discharge lamp apparatuses may be configured to operate the discharge lamps at the same time, in succession or in distinct operations of the apparatus/system. Operating multiple discharge lamps at the same time may advantageously reduce the time needed to treat an area. To further minimize the time needed to treat an area while preventing "overdosing" an area with too much UV light, an apparatus/system may be configured to modify operational parameters of the apparatus/system, such as the intensity or pulse frequency of each lamp, based on characteristics of the room in which the apparatus/system is arranged or on the ultraviolet light reflected from a target object. This may involve a database or one or more sensors, and sometimes a sensor for each discharge lamp unit, for determining characteristics of a room or the amount or intensity of ultraviolet light reflected from a target object. In some cases, an apparatus/system may include ultrasonic, infrared or other sensors to map a room in which the apparatus/system is arranged and, in some embodiments, be configured to map a room in relation to each discharge lamp unit. Such a mapping adaptation could also be included in an apparatus including a single discharge lamp which is not necessarily part of a multi-apparatus system.

In any case, a CPU of an apparatus/system may be configured to analyze the map/s and determine the necessary ultraviolet light dose in order to reach a minimum dose on all targeted surfaces. In addition, a CPU of a multi-lamp apparatus/system may be configured to allocate power to each discharge lamp unit to optimize the total treatment time for a room. The above could also be accomplished using feedback from sensors used to measure reflected ultraviolet light. Information from all sensors (e.g., ultraviolet light emitted, room size/shape, and position of all bulb units) could be fed into an equation or algorithm that determined a total operating time for each bulb unit. This would allow power to be diverted to units to optimize the decontamination speed in an area. For example, in a system configuration, two units may be used to treat different sections of an area or even different rooms. When sensors detect that one of the sections has received the required ultraviolet light dose, the corresponding unit could shut-off. The remaining unit could, in some embodiments, receive the diverted power and be able to pulse at a higher frequency if desired. The sensor system could be sophisticated enough to detect whether there was a common space between the different sections and further designate the second unit to treat the common space and therefore exclude that area from the dose calculations for the first unit. Additionally, operating time could be optimized by altering the directionality of emitted ultraviolet light for each bulb unit through changes in reflector height, orientation and/or shape.

In some embodiments, an apparatus or system could be created that moved within a room to provide multiple foci for ultraviolet light dispersal. In such cases, the information obtained through room sensing (via ultrasonic or infrared sensors or reflected ultraviolet light) could be used to guide a moving apparatus/system through a room. An apparatus/system could move using motorized wheels and have sensors to maneuver around obstacles. An apparatus/system could "learn" a room through sensing in real time as it moved, mapping the received dose on each surface as it moved. An apparatus/system could also be manually pushed through a room by a user while the apparatus/system mapped the room and then a CPU of the apparatus/system could analyze the map and determine the correct dose at each position for operation of the apparatus/system. The map and dose requirements could be used to alter the speed at which the mobile apparatus/system would pass by different surfaces.

Figure 10:
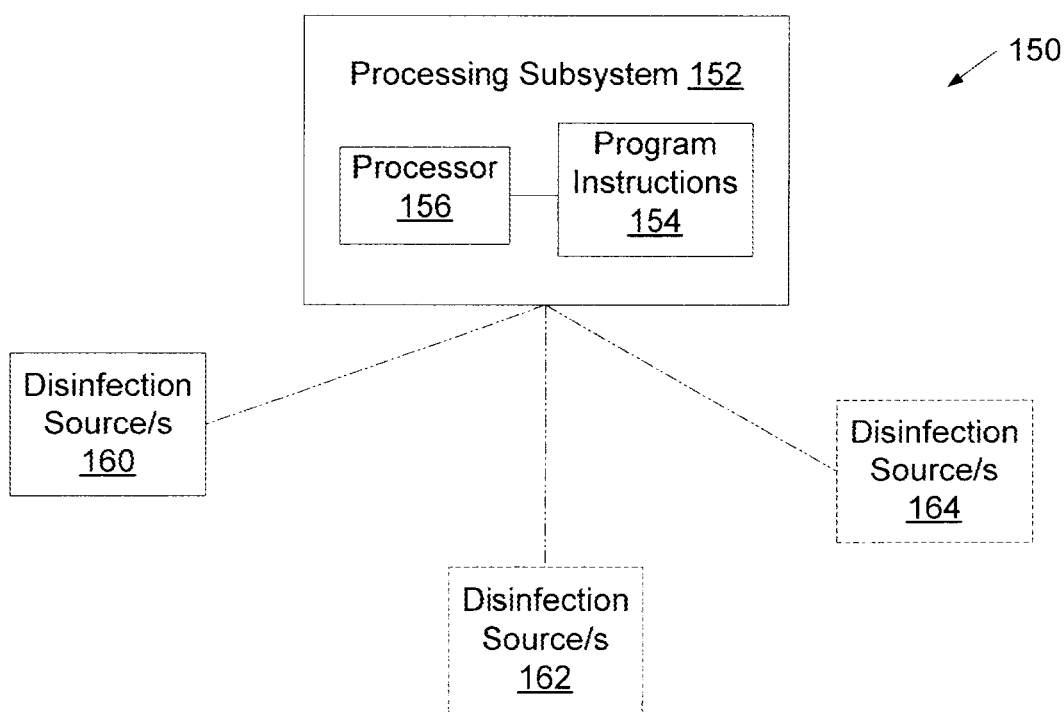
FIG. 10 depicts a system including one or more disinfection sources and a processing subsystem having processor-executable program instructions for determining operating parameters and disinfection schedules for one or more disinfection sources.
Figure 11:
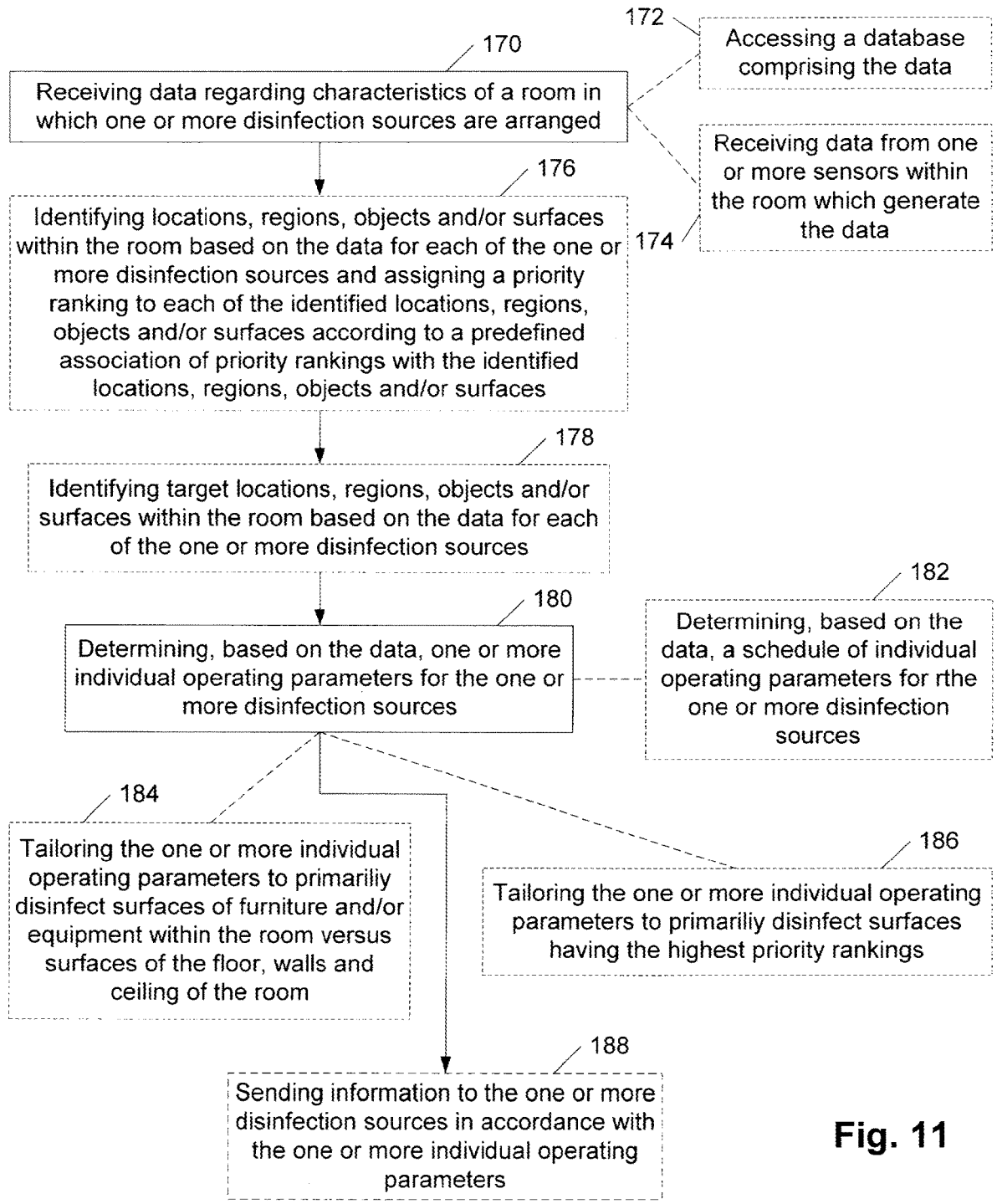
FIG. 11 depicts a flowchart outlining a method for which the processor-executable program instructions of the system depicted in FIG. 10 may be configured to perform.
Figure 12:
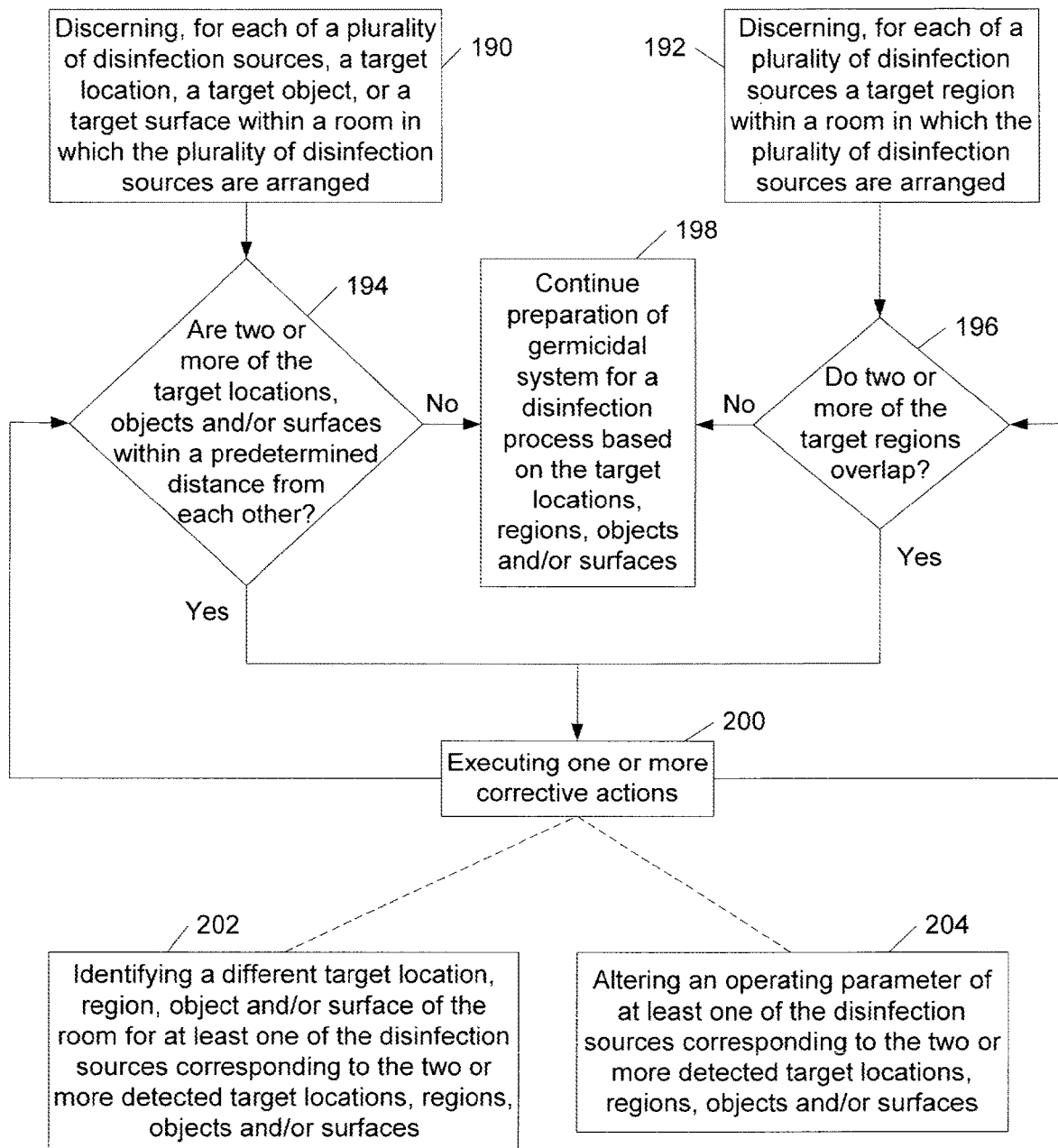
FIG. 12 depicts a flowchart outlining another method for which the processor-executable program instructions of the system depicted in FIG. 10 may be configured to perform.

Turning to FIGS. 10-12, systems for controlling the operation of germicidal devices and, more specifically, systems which determine operating parameters and disinfection schedules for germicidal devices are provided. In particular, FIG. 10 depicts a system including one or more disinfection sources and a processing subsystem having processor-executable program instructions for determining operating parameters and disinfection schedules for the one or more disinfection sources. In addition, FIG. 11 depicts a flowchart outlining a method for which the processor-executable program instructions of the system depicted in FIG. 10 may be configured to perform. Furthermore, FIG. 12 depicts a flowchart outlining another method for which the processor-executable program instructions of the system depicted in FIG. 10 may be configured to perform. In general, the systems and processes described in reference to FIGS. 10-12 may be applicable to any system including a disinfection source. The term "disinfection source" as used herein refers to a collection of one or more components used to generate and disperse a germicidal agent, and, if applicable, is inclusive to any additional components used to effect the generation or dispersal of the germicidal agent. In some embodiments, a device or an apparatus may include a single set of components for generating a germicide. In such cases, the components associated with generating the germicide may be referred to as the disinfection source or, alternatively, the device or apparatus as a whole may be referenced as a disinfection source. In other embodiments, a device or apparatus may include multiple disinfection sources (i.e., multiple sets of components for generating multiple sources of one or more germicides).

In any case, the term "germicide" as used herein refers to an agent for deactivating or killing microorganisms, particularly disease carrying and/or disease producing microorganisms (a.k.a., germs). The term "kill", as used herein, means to cause the death of an organism. In contrast, the term "deactivate", as used herein, means to render an organism unable to reproduce without killing. As such, a germicide which is configured to deactivate a microorganism refers to an agent which renders a microorganism unable to reproduce but leaves the organism alive. In general, the disinfection source's considered for the systems and processes disclosed in FIGS. 10-12 may be configured to generate a germicide in form of a liquid, a vapor, a gas, a plasma, ultraviolet light, and/or high-intensity narrow-spectrum (HINS) light. As such, the disinfection source/s considered or the systems and processes disclosed in FIGS. 10-12 may include but are not necessarily limited to the discharge lamp apparatuses described above in reference to FIGS. 1-9. Examples of disinfection sources which may be configured to disperse liquid, vapor, gaseous, or plasma germicides include but are not necessarily limited to liquid sprayers, foggers, plasmas torchers and misting systems including wet and dry mist systems. As used herein, the term "mist" refers to a suspension of minute globules of a liquid in a gas. For use herein, a germicidal mist is categorized as a liquid germicide.

In some embodiments, a liquid, vapor, gaseous or plasma germicide may impart its deactivation or killing functionality by the manner in which it is used. For example, boiling water, steam and heated air are often effective sterilizing agents due to the temperature at which they are employed. Furthermore, the germicidal effectiveness of some plasma germicides is primarily due to the presence and activity of charged particles making up the plasma rather than the molecular composition of the charged particles. As used herein, the phrase "molecularly configured" refers to the elemental composition of a substance (i.e., the number and type of atoms making up a substance) to impart the function stated after the phrase. In some cases, the functionality of a liquid, vapor, gaseous or plasma germicide to deactivate and/or kill a microorganism may be attributed to the elements constituting the germicide and, thus, such germicides may be referenced as being molecularly configured to deactivate and/or kill microorganisms.

An example of a gaseous germicide that is molecularly configured to kill microorganisms is ozone. Examples of plasmas germicides that are molecularly configured to deactivate or kill microorganisms are those that employ or generate reactive oxygen species. Examples of liquid and vapor germicides that are molecularly configured to deactivate or kill microorganisms include liquid and vapor disinfection solutions having a principle disinfection agent such as but not limited to bleach, hydrogen peroxide, chlorine, alcohol, quaternary ammonium compounds or ozone. In any of such cases, the liquid and vapor germicides may be aqueous or non-aqueous. It is noted that the disinfection source's considered or the systems and processes disclosed in FIGS. 10-12 may include those which are configured to impart deactivation or killing functionality by the manner in which the germicide is used as well as by a germicide's molecularly configuration.

Turning to FIG. 10, system 150 is shown including disinfection source's 160 and optionally disinfection source/s 162 and 164. In particular, the dotted lines bordering disinfection source's 162 and 164 denote that they are optional features of system 150. In general, system 150 may include any number of disinfection sources, including just one disinfection source or any plurality of disinfection sources. Furthermore, system 150 may include any number of devices or apparatuses including one or more disinfection sources. In particular, system 150 may, in some cases, include a single disinfection device or apparatus having one or more disinfection sources. In other embodiments, system 150 may include multiple disinfection devices or apparatuses each having one or more disinfection sources as shown in FIG. 10.

In any case, the disinfection source's within system 150 may be fixedly arranged within a room or may be portable. In embodiments in which system 150 includes multiple disinfection sources, less than all of the disinfection sources may be fixedly arranged within a room and the others may be portable. In yet other cases in which system 150 includes multiple disinfection sources, all of the disinfection sources may be fixedly arranged within a room or all may be portable. Furthermore, as noted above, the disinfection source's considered for the systems and processes disclosed in FIGS. 10-12 may be configured to generate a germicide in form of a liquid, a vapor, a gas, a plasma, ultraviolet light, and/or high-intensity narrow-spectrum (HINS) light. It is noted that in embodiments in which system 150 includes multiple disinfection sources, the disinfection source's may be any combination of sources configured to generate a germicide in form of a liquid, a vapor, a gas, a plasma, ultraviolet light, and/or high-intensity narrow-spectrum (HINS) light or may exclusively include the same type of disinfection source.

As set forth in more detail below, the processes outlined in FIGS. 11 and 12 for determining operating parameters and disinfection schedules for disinfection source/s 160 and optionally disinfection source/s 162 and 164 are based on characteristics of a room in which system 150 is arranged. Consequently, the disinfection source/s of system 150 as well as the device/s and apparatus/es comprising the disinfection source/s may be particularly configured for room disinfection. More specifically, the disinfection source's of system 150 as well as the device/s and apparatus/es comprising the disinfection source/s may be configured to distribute a germicidal agent in a spacious manner such that a room may be treated. As used herein, the term "room disinfection" refers to the cleansing of a bounded area which is suitable for human occupancy so as to deactivate, destroy or prevent the growth of disease-carrying microorganisms in the area. It is noted that the room disinfection devices and apparatuses described herein, particularly ones considered for the systems and processes described in reference to FIGS. 10-12, may come in a variety of configurations, including those which are floor based, wall based and ceiling based.

As further shown in FIG. 10, system 150 includes processing subsystem 152 having processor 156 and program instructions 154 which are executable by processor 156. As set forth in more detail below in reference to FIGS. 11 and 12, program instructions 154 may be configured to determine operating parameters and/or disinfection schedules for the disinfection sources comprising system 150 (e.g., disinfection source's 160 and, if applicable, disinfection source's 162 and 164). The term "program instructions", as used herein, may generally refer to commands within a program which are configured to perform a particular function, such as receiving input, recording receipts of signals, determining when and/or whether to allow a device to start an operation, and sending signals to start and/or end operation of a device. Program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. Program instructions implementing the processes described herein may be transmitted over on a carrier medium such as a wire, cable, or wireless transmission link.

In some embodiments, processing subsystem 152 may be a single processing unit which is connected to each of the disinfection source's of system 150 and, thus, may be considered a central processing unit, particularly when system 150 includes multiple disinfection sources. In such cases, processing subsystem 152 may, in some embodiments, be a distinct entity from the device/s or apparatus/es comprising the disinfection source's of system 150 as shown in FIG. 10. In yet other cases, processing subsystem 152 may be disposed within a device or apparatus comprising the disinfection source's of system 150. In yet other embodiments, processing subsystem 152 may include multiple processors, each disposed on a different device or apparatus comprising the disinfection source's of system 150. In such cases, processing subsystem 152 may be at least partially distributed among devices or apparatuses comprising the multiple disinfection sources. In some embodiments, each device or apparatus comprising disinfection source's of system 150 may include a processor and program instructions 154.

Turning to FIG. 11, a flowchart is provided outlining processes for determining one or more operating parameters for one or more disinfection sources of a germicidal system based upon characteristics of a room in which the one or more disinfection sources are arranged. As shown in block 170 of FIG. 11, the method includes receiving data regarding characteristics of a room in which one or more disinfection sources are arranged. Such a process may include accessing a database comprising the data as denoted in block 172 and/or receiving data from one or more sensors within the room which generate the data as denoted in block 174. In the latter case, the one or more sensors may, in some embodiments, be independent from the disinfection source/s and the processing subsystem of the germicidal system. In other cases, one or more of the sensors may be disposed within one or more of the disinfection source's or within the processing subsystem of the germicidal system if it is distinct from the disinfection source/s.

In general, the phrase "characteristics of a room" as used herein refers to physical attributes as well as non-physical attributes of a room. Non-physical attributes of a room include but are not necessarily limited to identifiers used to reference a room (e.g., room number and/or room name) and occupancy information regarding a room (e.g., infection information of a patient previously occupying the room or a patient scheduled to occupy the room). Physical attributes of a room include but are not necessarily limited to size and/or dimensions of the room and/or the number, size, distances, locations, reflectivity and/or identification or prioritization of surfaces and/or objects within the room. In some cases, a physical attribute of a room may be the identification (i.e., detection via sample analysis) of one or more pathological organisms and, sometimes further the number or concentration of such organism/s in the room, in a particular region of the room, or on a particular surface in the room.

As further shown in block 180 of FIG. 11, the method further includes determining one or more individual operating parameters for the one or more disinfection sources based on the data received regarding the characteristics of the room. The phrase "operating parameter of a disinfection source" as used herein refers to any parameter which may affect operation of a disinfection source, including but not limited to run time of a disinfection source, position of a disinfection source, orientation of components comprising a disinfection source, germicidal dosing parameters for the disinfection source, and/or power supplied to a disinfection source. In cases in which the disinfection source includes a pulsed germicidal source, such as a flashlamp for example, germicidal dosing parameters for the disinfection source may include pulse duration and/or pulse frequency. Furthermore, in embodiments in which the germicidal source is a flashlamp, power supplied to the flashlamp may be referred to as "pulse intensity" or "intensity of the lamp".

During the development of the systems described herein, a few discoveries arose while investigating optimum intensities and amounts of exposure of ultraviolet light from xenon flashbulbs. In particular, it was discovered that for a given microorganism at a set distance, there are diminishing returns to increasing the pulse intensity of a xenon flashlamp in regard to disinfection efficiency of the flashlamp. In other words, it was discovered that more intense pulses of a xenon flashlamp did not result in a proportional manner to a higher efficiency of disinfection for a given microorganism at a set distance. Hence, it is set forth that in some cases pulse intensities may be used for xenon flashlamps which are lower than those conventionally employed for disinfection processes including xenon flashlamps of comparable size (i.e., voltage application may be reduced, such as by up to approximately 25%). Such a reduction in pulse intensity will reduce energy use and extend bulb life, leading to cost savings. It is contemplated that there are diminishing returns to increasing the pulse intensity of other types of flashlamps regarding disinfection efficiency and, thus, it is set forth that lower pulse intensities may be applicable for any type of pulsed light source relative to those conventionally employed for the same type and size of pulsed light source.

It is noted that knowledge of the aforementioned discovery may be beneficial for the systems described herein, particularly for determining pulse intensity for a pulsed light disinfection source that conserves energy and lengthens bulb life but optimizes a disinfection process for a room. In particular, the systems described herein may be programmed with information correlating to the aforementioned discovery to determine a favorable (suitably disinfective, but energy conserving) pulse intensity for a pulsed light disinfection source based on characteristics of a room, such as size of the room, distance to an intended object from the pulsed light disinfection source, and/or disinfection of a target microorganism identified for the room.

Figure 13:
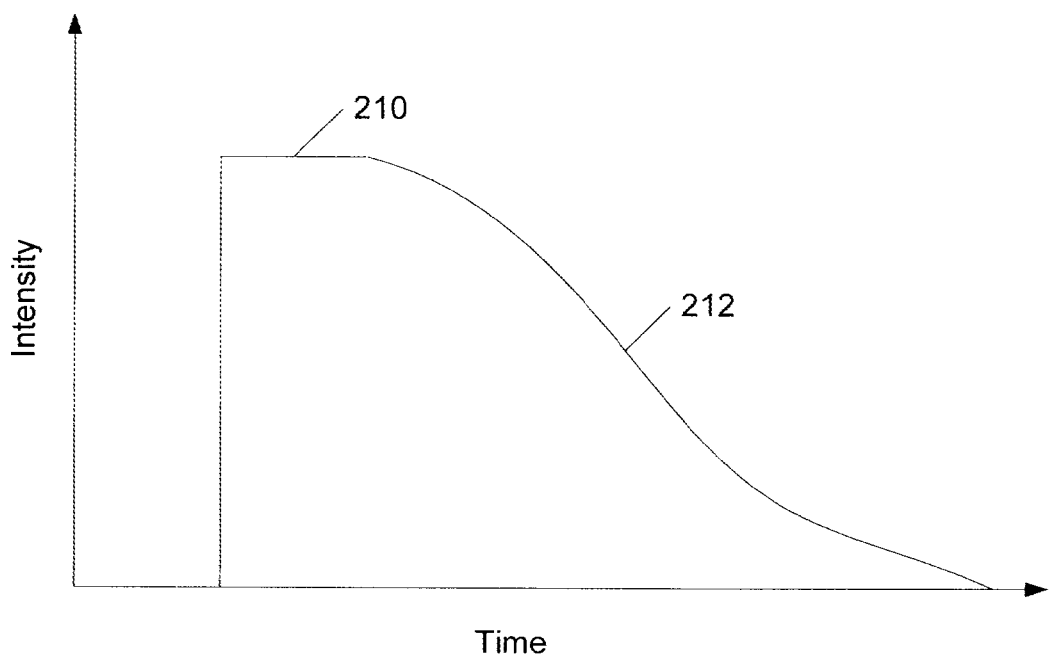
FIG. 13 depicts a graph of a xenon pulse profile having a tail portion descending from initial intensity level.
Figure 14:
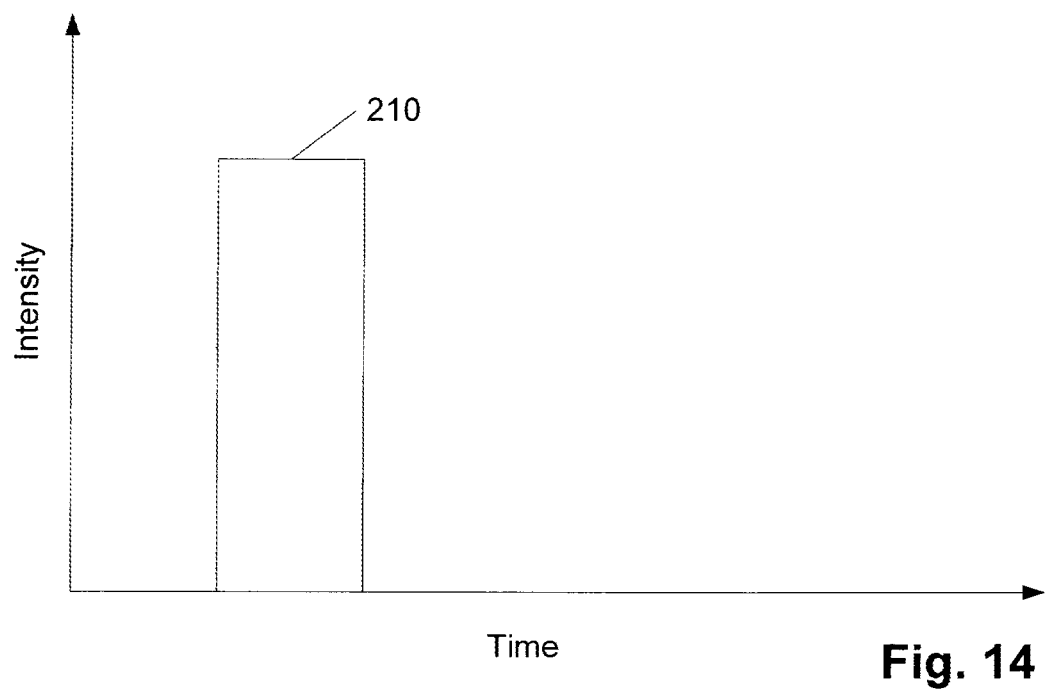
FIG. 14 depicts a graph a xenon pulse profile having same initial intensity level as the pulse profile depicted in FIG. 13 without a tail portion.

It was further discovered during the development of the systems described herein that eliminating the descending tail portion of a xenon pulse profile does not significantly impact the disinfection properties of the light generated by a xenon flashlamp. In particular, it was discovered that respective systems which generate xenon pulse profiles with and without a tail portion descending from a same level of initial intensity do not differ in disinfection efficacy. FIGS. 13 and 14 depict examples of xenon pulse profiles, respectively with and without a tail portion descending from a same level of the initial intensity for a xenon flashlamp. In particular, FIG. 13 illustrates a xenon pulse profile having tail portion 212 descending from intensity level 210. FIG. 14, on the other hand, illustrates a corresponding xenon pulse profile having same applied intensity level 210, but without tail portion 212. The reduction in microbial growth resulting from application of the xenon pulse profiles of FIGS. 13 and 14 were substantially similar, constituting the aforementioned discovery. In view of such a discovery, it is contemplated that reducing the descending tail portion rather than eliminating it will not significantly impact the disinfection properties of the light generated by a xenon flashlamp either. The xenon pulse profiles of FIGS. 13 and 14 were generated from the same system with a distinguishing factor that the xenon pulse profile of FIG. 14 was generated employing a smaller induction coil in the system than that what was employed for the xenon pulse profile of FIG. 13. It is noted that other manners may be employed for eliminating or reducing descending tail portions of a xenon pulse profile and, thus, generating xenon pulse profiles with a reduced or no descending tail portion are not necessarily limited to use of smaller induction coils in xenon flashlamp systems.

As a consequence of reducing or eliminating the descending tail portion of a xenon pulse profile, it is set forth that pulse durations of xenon flashlamps may be shortened relative to conventional disinfection processes employing xenon flashlamps of comparable size. A reduction in pulse duration will advantageously conserve energy, reducing costs of using a xenon flashlamp. It is set forth that pulse duration of a xenon flashlamp may be reduced by up to 75% relative to a conventional disinfection processes employing xenon flashlamps of comparable size. As an example, pulse durations of a xenon flashlamps considered for the systems described herein may be in the range of approximately 80 microseconds and approximately 120 microseconds. Shorter or longer pulse durations, however, may be employed. In light of the possibility of reduced pulse durations, it is further set forth that when the xenon pulse profiles are generated with a reduced or no descending tail portion, pulse frequencies of xenon flashlamps may be increased relative to current disinfection processes employing xenon flashlamps of comparable size. Higher pulse frequencies will increase the disinfection rate of a xenon flashlamp, improving the disinfection efficiency of a system. As a consequence of increasing pulse frequency, total durations of disinfection processes employing xenon flashlamps may be shortened relative to current disinfection processes employing xenon flashlamps of comparable size, saving time for conducting a disinfection process.

It is contemplated in light of the aforementioned discovery that reducing or eliminating the descending trail portions of pulse profiles of other types of flashlamps will not impact the disinfection properties of the light generated by the flashlamps. Thus, it is set forth that shortened pulse durations, increased pulse frequencies, and/or reduced durations for disinfection processes may be applicable for any type of pulsed light source relative to those conventionally employed for the same type and size of pulsed light source. It is further noted that knowledge of the aforementioned discovery may be beneficial for the systems described herein, particularly for determining pulse duration, pulse frequency, and/or run time for a pulsed light disinfection source. In particular, the systems described herein may be programmed with information correlating to the aforementioned discovery to determine a pulse duration which conserves energy, a pulse frequency which increases disinfection efficiency, and/or a run time which reduces the time for a disinfection process, all of which may be based on characteristics of a room.

In general, there are a number of manners in which to conduct the process outlined in block 180, i.e. to determine one or more individual operating parameters for the one or more disinfection sources based on the data received regarding the characteristics of the room. For example, the process may, in some embodiments, involve accessing a database comprising a list of room attributes and corresponding predetermined operating parameter/s for one or more disinfection sources. For instance, a non-physical attribute of a room, such as a room number, a room name or occupancy information regarding the room, may be entered into a user interface of a germicidal system and such data entry may initiate access to the aforementioned database to determine operating parameter/s for one or more disinfection sources. In particular, a preassigned room identifier (such as "103" or "Operating Room") may be entered into a user interface (such as by key entry or scanning a barcode) and one or more operating parameters for one or more disinfection sources arranged in such a room may be determined from a database outlining such correlative information. Such an embodiment may be particularly applicable for a germicidal system which includes one or more portable disinfection devices and, thus, are used within a plurality of different rooms. Another example includes entering in occupancy information regarding a room (e.g., infection information of a patient previously occupying the room or a patient scheduled to occupy the room) into a user interface one or more operating parameters for one or more disinfection sources may be determined from such information. Such an embodiment may be particularly applicable when a patient previously occupying a room was diagnosed and/or was treated for a specific spore infection or when an incoming patient who is known to have a low immune system (such as human immunodeficiency virus (HIV)). In such cases, the operating parameter determined for the one or more disinfection sources may be based on the patient's affliction.

In some cases, the aforementioned process may be augmented by factoring in the number and/or type of disinfection sources or devices arranged in the room. In particular, in addition to entering a non-physical attribute of a room, such as a room number, a room name or occupancy information regarding the room, into a user interface, the number and/or type of disinfection sources or devices arranged in the room may be entered into the user interface in order to determine one or more operating parameters of one or more disinfection sources. In such cases, the database accessed upon such entry may include additional field/s regarding numbers and/or types of disinfection sources which may be applicable for each room attribute listed and a corresponding different set of one or more operating parameters for each disinfection source. In some cases, particular disinfection sources may be selected for use based on characteristics of a room. It is noted that the aforementioned embodiments are not only applicable for germicidal systems having one or more portable disinfection devices exclusively, but are also applicable for germicidal systems having one or more portable disinfection devices in combination with disinfection sources fixedly disposed within a room. In the latter of such embodiments, the operating parameters set forth in the database may, in some cases, be preset based on known positions of the fixedly disposed disinfection sources in a room.

It is noted that accessing a database to determine one or more operating parameters of one or more disinfection sources is not limited to nonphysical attributes of a room (such as a room identifier or occupancy information for the room). In particular, a database may additionally or alternatively include a list of values or ranges for one or more physical attributes (such as size and/or dimensions of the room and/or the number, size, distances, locations, reflectivity and/or identification or prioritization of surfaces and/or objects within the room) and corresponding predetermined operating parameter/s for one or more disinfection sources which may be arranged in a room. Such an embodiment may also be augmented by factoring in the number and/or type of disinfection sources or devices arranged in the room to determine one or more operating parameters of the disinfection source/s.

In any case, the physical attributes may be entered via a user interface or may be obtained via one or more sensors within a room. An example of an embodiment which may be applicable for the aforementioned case is when a room size is obtained and an accessible database includes different run times, different rates of germicidal discharge, and/or different power levels to be supplied to disinfection sources for different room sizes or ranges of room sizes. In particular, relatively large rooms will likely need longer and/or more efficient germicidal exposure versus smaller rooms and, thus, it is contemplated that it would be advantageous to set run times, rates of germicidal discharge, and/or power levels to be supplied to disinfection sources based on a size of a room. In cases in which the disinfection source includes a pulsed germicidal source, such as a flashlamp for example, operating parameters affecting rates of germicidal discharge for the disinfection source may include pulse duration and/or pulse frequency. Furthermore, in embodiments in which the germicidal source is a flashlamp, power level supplied to the flashlamp may be referred to as "pulse intensity" or "intensity of the lamp". Other correlations of room characteristics to operating parameters of disinfection sources may be contemplated for a database and, thus, the aforementioned example is not to be construed as limiting the scope of the disclosure provided herein.

An alternative manner in which to determine one or more operating parameters of one or more disinfection sources based on characteristics of a room is to employ an algorithm correlating such variables. The algorithm may, in some embodiments, be based solely on physical characteristics of a room to determine one or more operating parameters of one or more disinfection sources. In other cases, the algorithm may be based on a combination of physical and nonphysical characteristics of a room to determine one or more operating parameters of one or more disinfection sources. In any embodiment, particular disinfection sources may be selected for use based on characteristics of a room, particularly via use of the algorithm, in addition or alternative to determining operating parameters of one or more disinfection sources. As with the database embodiments noted above, the algorithm may, in some embodiments, be based on the number and/or type of disinfection devices arranged in the room in addition to characteristics of the room. Although not necessarily so limited, it may be advantageous to employ an algorithm-based process when multiple room characteristics affect a determination of operating parameter/s for one or more disinfection sources. In addition or alternatively, it may be advantageous to employ an algorithm-based process when multiple operating parameters are to be determined and/or when individual operating parameter/s are to be determined for multiple disinfection sources. In particular, the scope of correlating variables becomes more complex as more variables play a role and, thus, an algorithm may be more suitable than a database in such cases.

In some cases, the room characteristic data received at block 170 of FIG. 11 may be used to identify locations, regions, objects and/or surfaces within the room as denoted in blocks 176 and 178. In such cases, the process of determining individual operating parameters for one or more disinfection sources denoted in block 180 may be based on the identified locations, regions, objects or surfaces of block 176 or block 178 (i.e., via a database or an algorithm). As noted in block 176, the room characteristic data received at block 170 may, in some embodiments, be used to identify locations, regions, objects and/or surfaces within the room and priority rankings (e.g., numbers or letters) may be assigned to each of the identified locations, regions, objects and/or surfaces according to a predefined association of priority rankings with the identified locations, regions, objects and/or surfaces (such as via a database or an algorithm). In some cases, the priority rankings for at least some of the surfaces may be based on an amount of time since their last disinfection. It is noted that the assignment of priority rankings in block 176 is one manner in which to incorporate prioritization to locations, regions, objects and/or surfaces within a room. Alternatively, priority rankings may be preassigned to locations, regions, objects and/or surfaces. In any case, the priority rankings may include any type of characters to denote a hierarchical importance among locations, regions, object and surfaces within a room, including but not limited to number, letters, and words such as "high" and "low."

As shown in FIG. 11, the priority characters assigned in block 176 may, in some embodiments, be used to identify target locations, regions, objects and/or surfaces within a room as denoted by the arrows between blocks 176 and 178. It is noted, however, that the dotted lines bordering blocks 176 and 178 denote that the processes are optional. As such, in some embodiments, block 176 may be omitted from the process and the room characteristic data received at block 170 may be used directly to identify target locations, regions, objects and/or surfaces within the room at block 178 (such as via a database or an algorithm). In other cases, block 178 may be omitted and the locations, regions, objects and/or surfaces identified in block 176 may be used to determine one or more individual operating parameters at block 180. In yet other embodiments, both blocks 176 and 178 may be omitted from the method and, thus, the process outlined in FIG. 11 may, in some cases, continue to block 180 directly from block 170. It is noted that in cases in which target locations, regions, objects and/or surfaces within a room are identified, the process of block 180 determines one or more operating parameters for each disinfection source specific to their targeted location/s, region/s, object/s and/or surface/s.

The process of identifying target locations, regions, objects and/or surfaces at block 178 may be implemented in a variety of manners and may generally be dependent on the type of sensor used to analyze a room for such targets. For example, in some cases, the targets may be identified by detection of the farthest distance from each disinfection source (i.e., using a distance sensor), i.e., the farthest distance to an object between apparatuses or the farthest distance from a disinfection source if no other apparatuses are detected in the vicinity. In other embodiments, targets may be identified by detection of the shortest distance from each disinfection source or detection of surfaces at a specified distance from each disinfection source. In alternative cases, a sensor may be used to evaluate the dimensions of objects and/or surfaces within a room and from such data the sensor and/or the processing subsystem of the germicidal system may be able to ascertain what the object and/or surface is (such as a bed, nightstand, or IV pole in a hospital room).

In some of such embodiments, targets may be selected based on the ascertained objects or surfaces. For example, in some cases, target regions may be identified based on the relatively high number of objects or surfaces in the region. In other embodiments, a target region may be identified based on one or more high priority objects and/or surfaces being in the region. Similarly, a target location, object or surface may be identified based the prioritization of locations, objects and/or surfaces within the room. In some cases, identifying a target location, region, object or surface may include identifying subsets of multiple locations, regions, objects or surfaces respectively arranged in vicinity of each disinfection source and designating a location, region, object or surface within each subset as a target. The designation process may be based on a number of different qualifiers, including but not limited to prioritization of the locations, regions, objects or surfaces and/or distance from each disinfection source.

There are a number of manners in which to craft a database and/or an algorithm for determining operating parameter/s for one or more disinfection sources. Some example manners are denoted in blocks 184 and 186 in FIG. 11. In particular, block 184 specifies tailoring the one or more individual operating parameters to primarily disinfect surfaces of furniture and/or equipment within the room versus surfaces of the floor, walls and ceiling of the room. In some of such cases, the process may further include determining one or more secondary operating parameters to primarily disinfect the floor, walls and/or ceiling of the room after the furniture and/or the equipment have been disinfected for a preset amount of time. In general, furniture and equipment within a room have a higher probability of having germs versus floors, walls and ceiling of the room and, thus, it may be advantageous to tailor a disinfection process to primarily disinfect those surfaces. In particular, invoking such precedence to a disinfection schedule may instigate a shorter and/or more efficient disinfection process or at least increase the likelihood that an adequate amount of disinfection has occurred if a disinfection process is terminated early.

As noted above, the region between approximately 2 feet and approximately 4 feet from a floor of a room is considered a "high touch" region of a room since objects of frequent use are generally placed in such a region. Due to such a region being considered a high touch zone, it is generally considered the area of highest probability to come in contact with germs and some studies indicate that the high touch zone may be the area having the highest concentration of germs. For such reasons, it may be advantageous to tailor one or more individual operating parameters to primarily disinfect surfaces of furniture and/or equipment which are in a region of a room between approximately 2 feet and approximately 4 feet from a floor of the room. In addition or alternatively, it may be advantageous to tailor one or more individual operating parameters among different furniture and/or equipment or even among different components of furniture and/or equipment. For example, a cabinet handle may warrant a higher and/or longer dosing of a germicidal agent versus a vertical face of a cabinet. Several other precedents among furniture, equipment and components may be considered as well for tailoring the operating parameters of disinfection sources, depending on the disinfection needs of the room being treated.

As shown in block 186 in FIG. 11, the process of block 180 may, in some embodiments, include tailoring the one or more individual operating parameters to primarily disinfect surfaces having the highest priority rankings, which may have been assigned in reference to block 176 or may have been preassigned to locations, regions, objects and/or surfaces within a room. Similar to the process of block 184, the process of block 186 invoking such precedence to a disinfection schedule may instigate a shorter and/or more efficient disinfection process or at least increase the likelihood that an adequate amount of disinfection has occurred if a disinfection process is terminated early. In some of such cases, the method may include determining one or more secondary operating parameters to primarily disinfect the surfaces having a lower priority ranking after surfaces having the highest priority ranking have been disinfected for a preset amount of time. Blocks 184 and 186 are outlined with dotted lines in FIG. 11 denoting that they are optional. In particular, many other manners may be used to tailor one or more operating parameters of one of more disinfection sources based on room characteristic data and, thus, the scope of the disclosure provided herein should not necessarily be limited to the depiction of FIG. 11.

As further shown in FIG. 11, the process may optionally include block 182 for determining a schedule of individual operating parameters for one or more disinfection sources. In such a context, the term "schedule" refers to a series of operating parameter designations to be performed in succession for one or more disinfection sources. As discussed in reference to the options for performing the process of block 180, determining a schedule of operating parameters may be based on primarily disinfecting furniture and equipment in a room and/or may be based on preassigned prioritization of locations, regions, object and/or surfaces within a room. Other manners may be used to tailor the schedule as well.

Regardless of the manner in which operating parameter/s of the one or more disinfection sources are determined, the process of FIG. 11 may, in some embodiments, include block 188 to send information to the one or more disinfection sources in accordance with the one or more individual operating parameters. The information may include individual run time/s for the disinfection source/s, a command to set or adjust individual rates of germicidal discharge from the disinfection source/s, and/or a common amount of power at which to operate the disinfection source/s. In yet other embodiments, individually specified amounts of power may be sent to disinfection sources in accordance with the determination process conducted in reference to block 180. In cases in which the disinfection source includes a pulsed germicidal source, such as a flashlamp for example, operating parameters affecting rates of germicidal discharge for the disinfection source may include pulse duration and/or pulse frequency. Furthermore, in embodiments in which the germicidal source is a flashlamp, power supplied to the flashlamp may be referred to as "pulse intensity" or "intensity of the lamp". In some cases, the information sent to the disinfection source's may be a position at which to place the disinfection source within the room and/or orientation/s of component/s comprising the disinfection source/s. In such cases, the disinfection device/s comprising the disinfection source/s may be configured to move and/or they may be able to move one or more of their components such that they may comply with the received information. Alternatively, the one or more operating parameters determined at block 180 may be displayed on a user interface and a user of the germicidal system may invoke the one or more operating parameters.

Embodiments of the method outlined in FIG. 11 which are considered to have particular application for room disinfection are set forth in detail below. Although such embodiments are described in detail and further enhancements are considered for them, the specific disclosure of such embodiments should not be construed to limit the scope of the disclosure set forth above in relation to FIG. 11.

A system which is considered to have particular application for room disinfection includes a disinfection source as well as a processing subsystem comprising a processor and program instructions which are executable by the processor for receiving data regarding physical attributes of a room in which the disinfection source is arranged. Such program instruction may be for accessing a database comprising the data and/or receiving data from one or more sensors of the system which generate the data. In either case, the processing subsystem includes program instructions executable by the processor for determining, based on the received data, a location within the room to position the disinfection source and/or an orientation of a component comprising the disinfection source. In some cases, the program instructions are further for determining, based on the data, a schedule of locations within the room to position the disinfection source and/or a schedule of orientations of one or more components comprising the disinfection source. In some embodiments, the disinfection source may be one of a plurality disinfection sources comprising the system. In such cases, the program instructions of the system may be executable by a processor for determining locations within the room to position each of the plurality of disinfection sources and/or determining orientations of one or more components of each of the plurality of disinfection sources.

The disinfection source/s in the aforementioned system may include a liquid, gas, vapor, plasma, ultraviolet light, and/or high-intensity narrow-spectrum (HINS) light disinfection source/s. In addition, the one or more component/s of the disinfection source/s which may be adjusted may include any moveable component of the disinfection source/s. Examples of moveable components of a light based disinfection source may include but are not limited to an optical filter comprising the disinfection source or any component of a reflector system or a lens system comprising the disinfection source, such as those described for the ultraviolet discharge lamp apparatuses shown in FIGS. 1-9. In some embodiments, a disinfection source may be configured to move relative to a device or apparatus comprising the disinfection source/s. An example of a possible configuration for a moveable disinfection source may be similar to a moveable spotlight having 180 degree movement capability or even up to nearly 360 degree movement capability. Other configurations of moveable disinfection sources may be considered. For example, a disinfection source may be configured to move along a track in some cases. In other embodiments, an entire device or apparatus comprising a disinfection source may be configured to move, particularly to a different location within a room.

In any case, in embodiments in which the disinfection source is configured to move itself and/or move one or more of its components, the processing subsystem may further include program instructions which are executable by a processor for sending information to the disinfection source to position itself to the determined location and/or arrange the component in the determined orientation. In yet other embodiments, the determined location and/or the determined component orientation may be displayed on a user interface and a user of the germicidal system may invoke the one or more operating parameters. In any case, a disinfection source which is considered to be particularly suitable for the aforementioned method is an ultraviolet light disinfection source having a repositionable reflector. The disclosure of such, however, should not be construed in any way to necessary limit the scope of the systems and/or methods described herein. In any case, the aforementioned system may have any of the configurations noted above in reference to FIGS. 10 and 11. As such, the system is not necessarily limited to receiving data regarding physical attributes of a room. In particular, the system may be configured to receive nonphysical attributes of a room as well. Furthermore, the system may include program instructions for determining any operating parameter of a disinfection source based on characteristics of a room. In particular, the aforementioned system is not necessarily limited to determining a location within the room to position a disinfection source and/or an orientation of a component comprising the disinfection source.

Another system which is considered to have particular application for room disinfection includes multiple disinfection sources and a processing subsystem comprising one or more processors and program instructions executable by the one or more processors for receiving data regarding the characteristics of a room in which the multiple disinfection sources are arranged. In addition, the program instructions are for determining, based on the data, one or more individual operating parameters for the multiple disinfection sources. In particular, the one or more individual operating parameters are specific for each of the disinfection sources. The one or more individual operating parameters may include run times of the disinfection sources, positions or speed of the disinfection sources within the room, orientation of components comprising the disinfection sources, rates of germicidal discharge from the disinfection sources and/or power supplied to the disinfection sources. In cases in which the disinfection sources include pulsed germicidal sources, such as a flashlamps for example, rates of germicidal discharge for the disinfection sources may include pulse duration and/or pulse frequency. Furthermore, in embodiments in which the germicidal sources include flashlamps, power supplied to the flashlamps may be referred to as "pulse intensity" or "intensity of the lamps". In some cases, the program instructions are further for determining, based on the data, a schedule of individual operating parameters for each of the multiple disinfection sources based on characteristics of the room. In general, the multiple disinfection sources may include liquid, gas, vapor, plasma, ultraviolet light, and/or high-intensity narrow-spectrum (HINS) light disinfection sources. The multiple disinfection sources may include the same type of disinfection source or may include a combination of disinfection sources at least some of which are different from each other. Furthermore, the aforementioned system may have any of the configurations noted above in reference to FIGS. 10 and 11.

A germicidal system which is considered to be particularly suitable for the aforementioned system is a light disinfection system having a plurality of light disinfection sources and further a power distribution means for distributing individual power requirements to each of the light disinfection sources as determined by the processing subsystem. Alternative to the power distribution means, each of the disinfection sources may include a power control circuit. In such cases, the processing subsystem may include processor-executable program instructions to send independent signals to the power control circuits to set the amount of power used to generate the light for each disinfection source. In either case, the different light disinfection sources may be distributed among different apparatuses, may be disposed on the same apparatus, or may be a combination thereof. Although the aforementioned light disinfection system is considered to be particularly suitable for room disinfection in which multiple disinfection sources are used, the disclosure of such should not be construed in any way to necessary limit the scope of the systems and/or methods described herein. In particular, it is asserted that other type of germicidal disinfection sources may be used in a similar system and/or a system may be configured with varied operating parameters other than power.

As set forth in more detail below in reference to FIG. 12, systems may, in some embodiments, be configured to have disinfection sources work in collaboration with each other, particularly regarding locations, regions, objects and/or surfaces the disinfection sources are targeted to disinfect. In some cases, the collaboration effort may involve distinct apparatuses communicating with each other. In particular, systems which include disinfection sources disposed on distinct apparatuses may be configured such that at least some of the apparatuses communicate with each other, particularly regarding their presence/location relative to each other and/or a location, region, object or surface their disinfection source/s are targeted to disinfect. More specifically, in some cases, the apparatuses may be configured to detect each other via a sensing system, such as but not limited to ultrasonic sensing or infrared sensing. In other embodiments, at least one apparatus may include a processor and program instructions executable by the processor for sending information regarding its location or a target location, region, object or surface of its disinfection source. As such, germicidal apparatuses of the systems described herein may be configured to know or be able to ascertain the presence or locations of other germicidal apparatuses in a room.

In cases in which an apparatus is configured to send information regarding the target location, region, object or surface of its disinfection source, another apparatus may include a processor and processor executable program instructions for receiving the information and comparing the received information with a target location, region, object or surface of its disinfection source. In addition or alternatively, however, the collaboration effort may involve comparing data at a central processing unit regarding targeted locations, regions, objects or surfaces of a plurality of disinfection sources. In either scenario, the systems may be configured to execute one or more correction actions upon detecting two or more locations, objects or surfaces are within a predetermined distance from each other or upon detecting two or more regions overlap as described in more detail below in reference to FIG. 12. In addition, the system may be configured to record areas which have been disinfected by the apparatuses during a course of a disinfection process such that those areas are deprioritized or not considered for disinfection for later stages of the disinfection process.

Turning to FIG. 12, a flowchart is shown outlining a method for which the processor-executable program instructions of the system depicted in FIG. 10 may be configured to perform. In particular, FIG. 12 outlines a method for collaborating information regarding targeted locations, regions, objects or surfaces of multiple disinfection sources and executing changes to the targeted locations, regions, objects or surfaces and/or to operating parameters of one or more of the disinfection sources upon detecting two or more locations, objects or surfaces are within a predetermined distance from each other or upon detecting two or more regions overlap. As shown in blocks 190 and 192 in FIG. 12, the method includes discerning, for each of a plurality of disinfection sources, a target location, region, object or surface within a room in which the plurality of disinfection sources are arranged. It is noted that the term "discerning" as used herein is inclusive to determining/identifying targeted locations, regions, objects or surfaces based on room characteristic data as described in reference to block 178 in FIG. 11, but is also inclusive to receiving the targeted locations, regions, objects or surfaces, such as by user input, barcode scanning, or accessing a database. In any case, at blocks 194 and 196, determinations are made whether two or more target locations, object or surfaces are within a predetermined distance from each other or whether two or more target regions overlap. The predetermined distance may be of any predetermined value and, in some cases, may be a threshold to indicate whether the target locations, objects, and surfaces are the same.

In cases in which the determination at block 194 or block 196 is "no", the method is directed to block 198 to continue preparation of the system for a disinfection process based on the target locations, regions, objects or surfaces identified for the disinfection sources. In some cases, the process of block 198 may include determining one or more individual operating parameters for each of the disinfection sources, such as described in reference to FIG. 11. In alternative embodiments, however, such a process may have been conducted prior to blocks 194 and 196. In some cases, the process of block 198 may include sending information to the disinfection sources in accordance with the individual operating parameters determined for each of the disinfection sources such as described in reference to block 188 in FIG. 11. In alternative embodiments, the process of block 198 may include one or more operating parameters being displayed on a user interface and a user of the germicidal system may invoke the one or more operating parameters.

In cases in which the determination at block 194 or block 196 is "yes", the method continues to block 200 to execute one or more corrective actions, particularly to change a planned disinfection process of at least one of the multiple disinfection sources. Blocks 202 and 204 are provided to offer examples of corrective actions which may be conducted, but other corrective actions may be considered. It is noted that blocks 202 and 204 may be both be performed for block 200 or just one of blocks 202 and 204 may be performed for block 200. As shown in block 202, one corrective action may be to identify a different target location, region, object or surface for at least one of the disinfection sources corresponding to the two or more detected target locations, regions, objects, and/or surfaces.

Another corrective action may be to alter an operating parameter of at least one of the disinfection sources corresponding to the two or more detected target locations, regions, objects, and/or surfaces as denoted in block 204. In such cases, the altered operating parameter may be a run time of the disinfection source, a position of the disinfection source within the room, an orientation of a component comprising the disinfection source, a rate of germicidal discharge from the disinfection source, and/or power supplied to the disinfection source. In cases in which the disinfection source includes a pulsed germicidal source, such as a flashlamp for example, operating parameter affecting rates of germicidal discharge for the disinfection source may include pulse duration and/or pulse frequency. Furthermore, in embodiments in which the germicidal source is a flashlamp, power supplied to the flashlamp may be referred to as "pulse intensity" or "intensity of the lamp". In some cases, operating parameters predetermined for the disinfection sources corresponding to two or more detected target locations, regions, objects, and/or surfaces may be compared prior to executing one or more corrective actions at block 200. In particular, in cases in which the determination at block 194 or block 196 is "yes", operating parameters predetermined for the disinfection sources may be compared and the comparison may factor in on the one or more corrective actions conducted in reference to block 200.

It is noted that although the processor-executable program instructions outlined in FIGS. 11 and 12 are described as being part a system including one or more disinfection sources, the processor-executable program instructions are not necessarily so restricted. In particular, the processor-executable program instructions outlined in FIGS. 11 and 12 may be disposed on a storage medium which is distinct and not necessarily associated with a particular germicidal system. More specifically, processor-executable program instructions outlined in FIGS. 11 and 12 may be distributed as software on a commercially viable storage medium for incorporation with one or more germicidal systems. In general, the term "storage medium", as used herein, may refer to any electronic medium configured to hold one or more set of program instructions, such as but not limited to a read-only memory, a random access memory, a magnetic or optical disk, or magnetic tape.

It will be appreciated to those skilled in the art having the benefit of this disclosure that germicidal lamp apparatuses are provided having one or more reflectors and/or one or more lenses for redirecting light emitted from the germicidal lamp. In addition systems are described which determine operating parameters and/or disinfection schedules for germicidal devices. In particular, the described systems are configured to work in a "smart" fashion (i.e., taking into consideration one or more characteristics of a room to determine operating parameters and/or disinfection schedules for germicidal devices). In some cases, the systems may be configured to optimize a disinfection process (e.g., time, efficiency, and thoroughness) for a room. Further modifications and alternative embodiments of various aspects of the apparatuses, systems and methods will be apparent to those skilled in the art in view of this description. For example, although the aforementioned discussions emphasize the configuration of ultraviolet discharge lamp apparatuses for disinfection purposes, the scope of this disclosure is not so limited. In particular, the ultraviolet discharge lamp apparatuses described herein may be used for any application utilizing ultraviolet light. In addition, the systems and processes described herein for determining operating parameters and disinfection schedules may be suitable for any germicidal system. Accordingly, this description is to be construed as illustrative only and is for the purpose of teaching those skilled in the art the general manner of carrying out the invention.

It is to be understood that the forms of the apparatuses, systems and methods shown and described herein are to be taken as the presently preferred embodiments. Elements and materials may be substituted for those illustrated and described herein, parts and processes may be reversed, and certain features of the apparatuses, systems and methods may be utilized independently, all as would be apparent to one skilled in the art after having the benefit of this disclosure. Changes may be made in the elements described herein without departing from the spirit and scope of the invention as described in the following claims.

What is claimed is:

1. A system, comprising:
multiple disinfection apparatuses each comprising at least one discharge lamp that is configured to emit ultraviolet light and a set of one or more sensors that are configured for detecting characteristics of an ambient exterior to its respective disinfection apparatus, wherein the multiple disinfection apparatuses are discrete devices unattached to each other, and wherein the characteristics detectable by the one or more sensors comprise:
  size and/or dimensions of a room in which the multiple disinfection apparatuses are arranged;
  a number, size, distance, location, reflectivity and/or identification of one or more surfaces and/or one or more objects within the room; and/or
  a number, concentration and/or identification of pathogens in the room, in a particular region of the room, or on a particular surface in the room; and
a processing subsystem comprising one or more processors and program instructions executable by the one or more processors for:
  receiving, from each set of one or more sensors of the multiple disinfection apparatuses, data regarding one or more detected characteristics of one or more areas in a room in relation to its disinfection apparatus;
  based on the received data, determining one or more operating parameters for each of the multiple disinfection apparatuses that are individual to each of the multiple disinfection apparatuses; and
  subsequent to determining the one or more operating parameters, activating operation of the multiple disinfection apparatuses and sending one or more commands to one or more means within each of the multiple disinfection apparatuses to automatically invoke the one or more operating parameters.

2. The system of claim 1, wherein the program instructions are further for activating the multiple disinfection apparatuses at the same time.

3. The system of claim 1, wherein the one or more operating parameters comprise run times for the multiple disinfection apparatuses, positions of the multiple disinfection apparatuses within the room, orientation of components comprising the multiple disinfection apparatuses, rates of germicidal discharge from the multiple disinfection apparatuses and/or power supplied to the multiple disinfection apparatuses.

4. The system of claim 1, wherein the program instructions for determining one or more operating parameters for the multiple disinfection apparatuses comprise program instructions for:
  identifying, based on the received data, a target location, region, surface or object within the room for each of the multiple disinfection apparatuses; and
  determining, for each of the multiple disinfection apparatuses, one or more individual operating parameters which are specific to disinfecting their target location, region, surface or object.

5. The system of claim 1, wherein each of the multiple disinfection apparatuses further comprise a reflector arranged to redirect light emitted from the lamp into an ambient of its respective disinfection apparatus and a means for providing movement of the reflector, and wherein the one or more operating parameters comprise movement characteristics of the reflectors of the multiple disinfection apparatuses during operation of the multiple disinfection apparatuses.

6. The system of claim 5, wherein the movement characteristics of the reflectors comprise continuous movement, periodic movement and/or timing of the movement of the reflectors.

7. The system of claim 5, wherein the discharge lamp of each of the multiple disinfection apparatuses is an elongated discharge lamp, wherein the reflector of each of the multiple disinfection apparatuses is an elongated rotatable reflector disposed along a side of the discharge lamp.

8. The system of claim 7, wherein the elongated discharge lamp and the elongated rotatable reflector of each of the multiple disinfection apparatuses are configured such that light emitted from the elongated discharge lamp during operation of the respective disinfection apparatus may collectively occupy an entirety of a region encircling the respective disinfection apparatus.

9. The system of claim 7, wherein the movement characteristics of the elongated rotatable reflectors comprise oscillating the elongated rotatable reflectors and/or rotating the elongated rotatable reflectors at least a full revolution.

10. A system, comprising:
multiple disinfection apparatuses each comprising at least one discharge lamp that is configured to emit ultraviolet light and a set of one or more sensors that are configured for detecting physical characteristics of an ambient exterior to its respective disinfection apparatus, wherein the multiple disinfection apparatuses are discrete devices unattached to each other, and wherein the physical characteristics comprise:
  size of a room in which the multiple disinfection apparatuses are arranged; and/or
  a number, size and/or distance of one or more objects within the room; and
a processing subsystem comprising one or more processors and program instructions executable by the one or more processors for:
  receiving, from each set of one or more sensors of the multiple disinfection apparatuses, data regarding physical characteristics of one or more areas in the room in relation to its disinfection apparatus;
  based on the received data, determining one or more operating parameters for each of the multiple disinfection apparatuses that are individual to each of the multiple disinfection apparatuses; and
  subsequent to determining the one or more operating parameters, sending one or more commands to one or more means within each of the multiple disinfection apparatuses to automatically invoke the one or more operating parameters.

11. The system of claim 10, wherein the one or more operating parameters comprise run times for the multiple disinfection apparatuses, positions of the multiple disinfection apparatuses within the room, orientation of components comprising the multiple disinfection apparatuses, rates of germicidal discharge from the multiple disinfection apparatuses and/or power supplied to the multiple disinfection apparatuses.

12. The system of claim 10, wherein the program instructions are further activating operation of the multiple disinfection apparatuses subsequent to determining the one or more operating parameters.

13. The system of claim 10, wherein each of the multiple disinfection apparatuses further comprise a reflector arranged to redirect light emitted from the lamp into an ambient of its respective disinfection apparatus and a means for providing movement of the reflector, and wherein the one or more operating parameters comprise movement characteristics of the reflectors of the multiple disinfection apparatuses during operation of the multiple disinfection apparatuses.

14. The system of claim 13, wherein the discharge lamp of each of the multiple disinfection apparatuses is an elongated discharge lamp, wherein the reflector of each of the multiple disinfection apparatuses is an elongated rotatable reflector disposed along a side of the discharge lamp.

15. A system, comprising:
multiple disinfection apparatuses each comprising at least one discharge lamp that is configured to emit ultraviolet light and a set of one or more sensors configured to map at least a portion room in relation to its respective disinfection apparatus, wherein the multiple disinfection apparatuses are discrete devices unattached to each other; and
a processing subsystem comprising one or more processors and program instructions executable by the one or more processors for:
receiving mapping data from each set of one or more sensors;
based on the received mapping data, determining one or more operating parameters for each of the multiple disinfection apparatuses that are individual to each of the multiple disinfection apparatuses; and
subsequent to determining the one or more operating parameters, sending one or more commands to one or more means within each of the multiple disinfection apparatuses to automatically invoke the one or more operating parameters.

16. The system of claim 15, wherein the one or more operating parameters comprise run times for the multiple disinfection apparatuses, positions of the multiple disinfection apparatuses within the room, orientation of components comprising the multiple disinfection apparatuses, rates of germicidal discharge from the multiple disinfection apparatuses and/or power supplied to the multiple disinfection apparatuses.

17. The system of claim 15, wherein the program instructions are further activating operation of the multiple disinfection apparatuses subsequent to determining the one or more operating parameters.

18. The system of claim 15, wherein each of the multiple disinfection apparatuses further comprise a reflector arranged to redirect light emitted from the lamp into an ambient of its respective disinfection apparatus and a means for providing movement of the reflector, and wherein the one or more operating parameters comprise movement characteristics of the reflectors of the multiple disinfection apparatuses during operation of the multiple disinfection apparatuses.

19. The system of claim 18, wherein the discharge lamp of each of the multiple disinfection apparatuses is an elongated discharge lamp, wherein the reflector of each of the multiple disinfection apparatuses is an elongated rotatable reflector disposed along a side of the discharge lamp.

20. The system of claim 13, wherein the movement characteristics of the reflectors comprise continuous movement, periodic movement and/or timing of the movement of the reflectors.

21. The system of claim 14, wherein the elongated discharge lamp and the elongated rotatable reflector of each of the multiple disinfection apparatuses are configured such that light emitted from the elongated discharge lamp during operation of the respective disinfection apparatus may collectively occupy an entirety of a region encircling the respective disinfection apparatus.

22. The system of claim 14, wherein the movement characteristics of the elongated rotatable reflectors comprise oscillating the elongated rotatable reflectors and/or rotating the elongated rotatable reflectors at least a full revolution.

* * * * *